US006372429B1

(12) United States Patent
Sharon

(10) Patent No.: US 6,372,429 B1
(45) Date of Patent: Apr. 16, 2002

(54) METHOD FOR ASSEMBLY OF MULTIPLE DNA FRAGMENTS

(75) Inventor: Gil Sharon, Mevasseret Zion (IL)

(73) Assignee: Gesher Israel Advanced Biotecs (1996) Ltd. (IL)

( * ) Notice: Subject to any disclaimer, the term of this patent is extended or adjusted under 35 U.S.C. 154(b) by 0 days.

(21) Appl. No.: 09/383,143

(22) Filed: Aug. 25, 1999

Related U.S. Application Data

(63) Continuation of application No. PCT/IL98/00096, filed on Feb. 26, 1998.

(30) Foreign Application Priority Data

Feb. 27, 1997 (IL) .................................................. 120339

(51) Int. Cl.$^7$ .......................... C12Q 1/68; C07H 21/02; C07H 21/04

(52) U.S. Cl. .......................... 435/6; 536/23.1; 536/24.3; 536/25; 536/25.3

(58) Field of Search .......................... 435/6, 91.1, 91.2, 435/183; 536/23.1, 24.3, 25, 25.3

(56) References Cited

U.S. PATENT DOCUMENTS

| 4,683,195 A | * | 7/1987 | Mullis et al. ................... 435/6 |
| 5,137,814 A | | 8/1992 | Rashtchian et al. ............ 435/91 |
| 5,580,759 A | * | 12/1996 | Yang et al. ................. 435/91.1 |

FOREIGN PATENT DOCUMENTS

EP        0 385410        9/1990

OTHER PUBLICATIONS

Aslanidis et al., "Minimal Length Requirement of the Single-stranded Tails for Ligation–independent Cloning (LIC) of PCR Products," PCR Methods and Applications, 1994, vol. 4, pp. 172–177.*
Oliner et al., "In vivo cloning of PCR products in *E. coli*," Nucleic Acids Reearch, 1993, vol. 21, No. 22, pp. 5192–5197.*
Aslanidis et al., "Minimal Length Requirement of the Single-stranded Tails for Ligation–independent Cloninc (LIC) of PCR products," PCR Methods and Applications, vol. 4, 1994, pp. 172–177.*
Kuijper, et al., Gene 112:147–155 (1992).
Oliner, et al., Nucleic Acids Research 21(22):5192–5197.
Roychoudhury, Gene Amplif. Anal., 2:41–83 (1981).
Rashtchian, et al., Anal. Biochem., 206(1):91–97 (1992).
Kuijper, et al., Gene, 112:147–155 (1992).
Booth, et al., Gene 146(2):303–308 (1994).
Smith, et al., PCR Methods & Applications 2(4):328–332 (1993).
Aslandis, et al., PCR Methods Appl., 4:172–177 (1994).
Hsiao, et al., Nucl. Acids Res., 21:5528–5529 (1993).
Yang, et al., Nucl. Acids Res., 21:1889–1893 (1993).

* cited by examiner

Primary Examiner—Bradley L. Sisson
(74) Attorney, Agent, or Firm—Lerner, David, Littenberg, Krumholz & Mentlik, LLP

(57) ABSTRACT

Methods for assembling two or more DNA fragments are disclosed including providing for each of the DNA fragments at least one protruding terminus or overhang capable of hydrogen bonding to a complementary sequence on at least one strand of a second DNA fragment, the overhang and the complementary sequence having at least 15 bases, and mixing two or more of the DNA fragments under conditions suitable to promote joining thereof. DNA constructs are also disclosed which are produced by joining two or more DNA fragments comprising at least one protruding terminus overhang capable of hydrogen bonding to a complementary sequence on at least one strand of a second DNA fragment.

21 Claims, 14 Drawing Sheets

FIG. 7
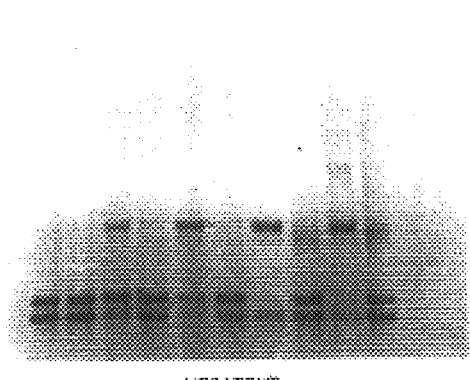
NEGATIVE
POSITIVE

FIG. 9
1.  
Number of Amp, Tet, Cm resistant transformants  
1st experiment  
2nd experiment
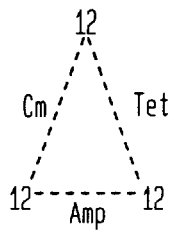
0  
0
4.  
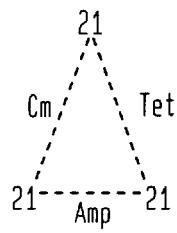
3  
280
2.  
Number of Amp, Tet, Cm resistant transformants  
1st experiment  
2nd experiment
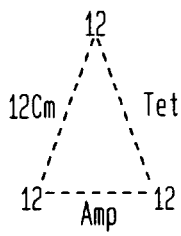
0  
6*
5.  
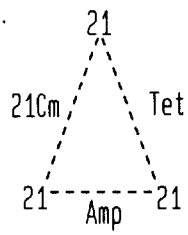
7  
108
3.  
Number of Amp, Tet, Cm resistant transformants  
1st experiment  
2nd experiment
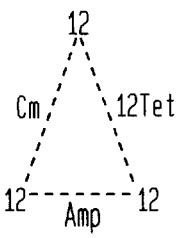
0  
0
6.  
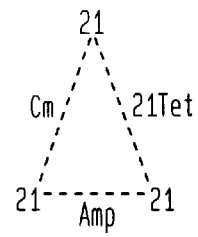
2  
2

SEQUENCE LISTING

<160> NUMBER OF SEQ ID NOS: 50

<210> SEQ ID NO 1
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 1
agctcctgat tctcatgttt gacagcttat c                                    31

<210> SEQ ID NO 2
<211> LENGTH: 37
<212> TYPE: DNA
<213> ORGANISM: Artificial Sequence
<220> FEATURE:
<223> OTHER INFORMATION: Description of Combined DNA/RNA Molecule:
      Primer

<400> SEQUENCE: 2
cuacuacuac uatggccagg acccaacgct gcccgag                              37

<210> SEQ ID NO 3
<211> LENGTH: 40
<212> TYPE: DNA
<213> ORGANISM: Artificial Sequence
<220> FEATURE:
<223> OTHER INFORMATION: Description of Combined DNA/RNA Molecule:
      Primer

<400> SEQUENCE: 3
cuacuacuac uacuatggcc aggacccaac gctgcccgag                           40

<210> SEQ ID NO 4
<211> LENGTH: 43
<212> TYPE: DNA
<213> ORGANISM: Artificial Sequence
<220> FEATURE:
<223> OTHER INFORMATION: Description of Combined DNA/RNA Molecule:
      Primer

<400> SEQUENCE: 4
cuacuacuac uacuacuaug gccaggaccc aacgctgccc gag                       43

<210> SEQ ID NO 5
<211> LENGTH: 46
<212> TYPE: DNA
<213> ORGANISM: Artificial Sequence
<220> FEATURE:
<223> OTHER INFORMATION: Description of Combined DNA/RNA Molecule:
      Primer

<400> SEQUENCE: 5
cuacuacuac uacuacuacu atggccagga cccaacgctg cccgag                    46

<210> SEQ ID NO 6
<211> LENGTH: 55
<212> TYPE: DNA
<213> ORGANISM: Artificial Sequence
<220> FEATURE:
<223> OTHER INFORMATION: Description of Combined DNA/RNA Molecule:
      Primer

<400> SEQUENCE: 6

-continued cuacuacuac uacuacuacu acuacuacua tggccaggac ccaacgctgc ccgag        55

<210> SEQ ID NO 7
<211> LENGTH: 41
<212> TYPE: DNA
<213> ORGANISM: Artificial Sequence
<220> FEATURE:
<223> OTHER INFORMATION: Description of Artificial Sequence: Primer

<400> SEQUENCE: 7
attggtgccc ttaaacgcct gaacgcagga agaacatgt g                       41

<210> SEQ ID NO 8
<211> LENGTH: 36
<212> TYPE: DNA
<213> ORGANISM: Artificial Sequence
<220> FEATURE:
<223> OTHER INFORMATION: Description of Combined DNA/RNA Molecule:
      Primer

<400> SEQUENCE: 8
uaguaguagu agaagagtat gagtattcaa catttc                            36

<210> SEQ ID NO 9
<211> LENGTH: 39
<212> TYPE: DNA
<213> ORGANISM: Artificial Sequence
<220> FEATURE:
<223> OTHER INFORMATION: Description of Combined DNA/RNA Molecule:
      Primer

<400> SEQUENCE: 9
uaguaguagu aguagaagag tatgagtatt caacatttc                         39

<210> SEQ ID NO 10
<211> LENGTH: 42
<212> TYPE: DNA
<213> ORGANISM: Artificial Sequence
<220> FEATURE:
<223> OTHER INFORMATION: Description of Combined DNA/RNA Molecule:
      Primer

<400> SEQUENCE: 10
uaguaguagu aguaguagaa gagtatgagt attcaacatt tc                     42

<210> SEQ ID NO 11
<211> LENGTH: 45
<212> TYPE: DNA
<213> ORGANISM: Artificial Sequence
<220> FEATURE:
<223> OTHER INFORMATION: Description of Combined DNA/RNA Molecule:
      Primer

<400> SEQUENCE: 11
uaguaguagu aguaguagua gaagagtatg agtattcaac atttc                  45

<210> SEQ ID NO 12
<211> LENGTH: 54
<212> TYPE: DNA
<213> ORGANISM: Artificial Sequence
<220> FEATURE:
<223> OTHER INFORMATION: Description of Combined DNA/RNA Molecule:
      Primer

<400> SEQUENCE: 12
uaguaguagu aguaguagua guaguaguag aagagtatga gtattcaaca tttc        54

<210> SEQ ID NO 13
<211> LENGTH: 37
<212> TYPE: DNA
<213> ORGANISM: Artificial Sequence
<220> FEATURE:
<223> OTHER INFORMATION: Description of Combined DNA/RNA Molecule:
      Primer

<400> SEQUENCE: 13
aucauaucau auttctcatg tttgacagct tatcatc                              37

<210> SEQ ID NO 14
<211> LENGTH: 38
<212> TYPE: DNA
<213> ORGANISM: Artificial Sequence
<220> FEATURE:
<223> OTHER INFORMATION: Description of Combined DNA/RNA Molecule:
      Primer

<400> SEQUENCE: 14
caucaucauc aucaggcgtt taagggcacc aataactg                             38

<210> SEQ ID NO 15
<211> LENGTH: 37
<212> TYPE: DNA
<213> ORGANISM: Artificial Sequence
<220> FEATURE:
<223> OTHER INFORMATION: Description of Combined DNA/RNA Molecule:
      Primer

<400> SEQUENCE: 15
uacuauacua uacatgccgg cgataatggc ctgcttc                              37

<210> SEQ ID NO 16
<211> LENGTH: 37
<212> TYPE: DNA
<213> ORGANISM: Artificial Sequence
<220> FEATURE:
<223> OTHER INFORMATION: Description of Combined DNA/RNA Molecule:
      Primer

<400> SEQUENCE: 16
uauaguauag uagtagatga cgaccatcag ggacagc                              37

<210> SEQ ID NO 17
<211> LENGTH: 37
<212> TYPE: DNA
<213> ORGANISM: Artificial Sequence
<220> FEATURE:
<223> OTHER INFORMATION: Description of Combined DNA/RNA Molecule:
      Primer

<400> SEQUENCE: 17
aucuaaucua autacggtga aaacctggcc tatttcc                              37

<210> SEQ ID NO 18
<211> LENGTH: 36
<212> TYPE: DNA
<213> ORGANISM: Artificial Sequence
<220> FEATURE:
<223> OTHER INFORMATION: Description of Combined DNA/RNA Molecule:
      Primer

<400> SEQUENCE: 18
augaugauga ugaacgcagg aaagaacatg tgagca                               36

<210> SEQ ID NO 19
<211> LENGTH: 45
<212> TYPE: DNA
<213> ORGANISM: Artificial Sequence
<220> FEATURE:
<223> OTHER INFORMATION: Description of Combined DNA/RNA Molecule:
      Primer

<400> SEQUENCE: 19
cauaucauau cauaucauau ttctcatgtt tgacagctta tcatc                    45

<210> SEQ ID NO 20
<211> LENGTH: 47
<212> TYPE: DNA
<213> ORGANISM: Artificial Sequence
<220> FEATURE:
<223> OTHER INFORMATION: Description of Combined DNA/RNA Molecule:
      Primer

<400> SEQUENCE: 20
caucaucauc aucaucauca ucaggcgttt aagggcacca ataactg                  47

<210> SEQ ID NO 21
<211> LENGTH: 45
<212> TYPE: DNA
<213> ORGANISM: Artificial Sequence
<220> FEATURE:
<223> OTHER INFORMATION: Description of Combined DNA/RNA Molecule:
      Primer

<400> SEQUENCE: 21
cuauacuaua cuauacuaua catgccggcg ataatggcct gcttc                    45

<210> SEQ ID NO 22
<211> LENGTH: 45
<212> TYPE: DNA
<213> ORGANISM: Artificial Sequence
<220> FEATURE:
<223> OTHER INFORMATION: Description of Combined DNA/RNA Molecule:
      Primer

<400> SEQUENCE: 22
uauaguauag uauaguauag gtagatgacg accatcaggg acagc                    45

<210> SEQ ID NO 23
<211> LENGTH: 45
<212> TYPE: DNA
<213> ORGANISM: Artificial Sequence
<220> FEATURE:
<223> OTHER INFORMATION: Description of Combined DNA/RNA Molecule:
      Primer

<400> SEQUENCE: 23
augaugauga ugaugaugau gaacgcagga aagaacatgt gagca                    45

<210> SEQ ID NO 24
<211> LENGTH: 45
<212> TYPE: DNA
<213> ORGANISM: Artificial Sequence
<220> FEATURE:
<223> OTHER INFORMATION: Description of Combined DNA/RNA Molecule:
      Primer

<400> SEQUENCE: 24
augaugauga ugaugaugau gaacgcagga aagaacatgt gagca                    45

<210> SEQ ID NO 25

```
<211> LENGTH: 37
<212> TYPE: DNA
<213> ORGANISM: Artificial Sequence
<220> FEATURE:
<223> OTHER INFORMATION: Description of Combined DNA/RNA Molecule:
      Primer

<400> SEQUENCE: 25
auaugauaug autcaggagc taaggaagct aaaatgg                              37

<210> SEQ ID NO 26
<211> LENGTH: 37
<212> TYPE: DNA
<213> ORGANISM: Artificial Sequence
<220> FEATURE:
<223> OTHER INFORMATION: Description of Combined DNA/RNA Molecule:
      Primer

<400> SEQUENCE: 26
auuagauuag aucaggcggg caagaatgtg aataaag                              37

<210> SEQ ID NO 27
<211> LENGTH: 45
<212> TYPE: DNA
<213> ORGANISM: Artificial Sequence
<220> FEATURE:
<223> OTHER INFORMATION: Description of Combined DNA/RNA Molecule:
      Primer

<400> SEQUENCE: 27
auaugauaug auaugauaug tcaggagcta aggaagctaa aatgg                     45

<210> SEQ ID NO 28
<211> LENGTH: 45
<212> TYPE: DNA
<213> ORGANISM: Artificial Sequence
<220> FEATURE:
<223> OTHER INFORMATION: Description of Combined DNA/RNA Molecule:
      Primer

<400> SEQUENCE: 28
auuagauuag auuagauuag caggcgggca agaatgtgaa taaag                     45

<210> SEQ ID NO 29
<211> LENGTH: 41
<212> TYPE: DNA
<213> ORGANISM: Artificial Sequence
<220> FEATURE:
<223> OTHER INFORMATION: Description of Artificial Sequence: Primer

<400> SEQUENCE: 29
attggtgccc ttaaacgcct gaacgcagga aagaacatgt g                        41

<210> SEQ ID NO 30
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 30
agcgttgggt cctggccaaa gagtatgagt attcaaca                            38

<210> SEQ ID NO 31
<211> LENGTH: 31
<212> TYPE: DNA
<213> ORGANISM: Artificial Sequence
```

```
<220> FEATURE:
<223> OTHER INFORMATION: Description of Artificial Sequence: Primer

<400> SEQUENCE: 31
agctcctgat tctcatgttt gacagcttat c                              31

<210> SEQ ID NO 32
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 32
atactctttg gccaggaccc aacgctgccc                                30

<210> SEQ ID NO 33
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 33
aaacatgaga tcaggagct aaggaagcta aaatg                           35

<210> SEQ ID NO 34
<211> LENGTH: 41
<212> TYPE: DNA
<213> ORGANISM: Artificial Sequence
<220> FEATURE:
<223> OTHER INFORMATION: Description of Artificial Sequence: Primer

<400> SEQUENCE: 34
atgttctttc ctgcgttcag gcgtttaagg gcaccaataa c                   41

<210> SEQ ID NO 35
<211> LENGTH: 24
<212> TYPE: DNA
<213> ORGANISM: Artificial Sequence
<220> FEATURE:
<223> OTHER INFORMATION: Description of Combined DNA/RNA Molecule:
      Primer

<400> SEQUENCE: 35
attgctgcag gcatcgtggt guca                                      24

<210> SEQ ID NO 36
<211> LENGTH: 36
<212> TYPE: DNA
<213> ORGANISM: Artificial Sequence
<220> FEATURE:
<223> OTHER INFORMATION: Description of Combined DNA/RNA Molecule:
      Primer

<400> SEQUENCE: 36
agcgttgggt cctggccaaa gagtaugagt attcaa                         36

<210> SEQ ID NO 37
<211> LENGTH: 27
<212> TYPE: DNA
<213> ORGANISM: Artificial Sequence
<220> FEATURE:
<223> OTHER INFORMATION: Description of Combined DNA/RNA Molecule:
      Primer

<400> SEQUENCE: 37
```
acgcctgaac gcaggaaaga acaugtg 27

<210> SEQ ID NO 38
<211> LENGTH: 24
<212> TYPE: DNA
<213> ORGANISM: Artificial Sequence
<220> FEATURE:
<223> OTHER INFORMATION: Description of Combined DNA/RNA Molecule:
      Primer

<400> SEQUENCE: 38
acaccacgat gcctgcagca augg 24

<210> SEQ ID NO 39
<211> LENGTH: 40
<212> TYPE: DNA
<213> ORGANISM: Artificial Sequence
<220> FEATURE:
<223> OTHER INFORMATION: Description of Combined DNA/RNA Molecule:
      Primer

<400> SEQUENCE: 39
aggcctggta tgagtctcag gagcuaagga agctaaaatg 40

<210> SEQ ID NO 40
<211> LENGTH: 27
<212> TYPE: DNA
<213> ORGANISM: Artificial Sequence
<220> FEATURE:
<223> OTHER INFORMATION: Description of Combined DNA/RNA Molecule:
      Primer

<400> SEQUENCE: 40
attggctgag acgaaaaaca tautctc 27

<210> SEQ ID NO 41
<211> LENGTH: 25
<212> TYPE: DNA
<213> ORGANISM: Artificial Sequence
<220> FEATURE:
<223> OTHER INFORMATION: Description of Combined DNA/RNA Molecule:
      Primer

<400> SEQUENCE: 41
atatgttttt cgtctcagcc aaucc 25

<210> SEQ ID NO 42
<211> LENGTH: 41
<212> TYPE: DNA
<213> ORGANISM: Artificial Sequence
<220> FEATURE:
<223> OTHER INFORMATION: Description of Combined DNA/RNA Molecule:
      Primer

<400> SEQUENCE: 42
atgttctttc ctgcgttcag gcguttaagg gcaccaataa c 41

<210> SEQ ID NO 43
<211> LENGTH: 27
<212> TYPE: DNA
<213> ORGANISM: Artificial Sequence
<220> FEATURE:
<223> OTHER INFORMATION: Description of Combined DNA/RNA Molecule:
      Primer

<400> SEQUENCE: 43
ataccgcaag cgacaggccg aucatcg                                                   27

<210> SEQ ID NO 44
<211> LENGTH: 36
<212> TYPE: DNA
<213> ORGANISM: Artificial Sequence
<220> FEATURE:
<223> OTHER INFORMATION: Description of Combined DNA/RNA Molecule:
      Primer

<400> SEQUENCE: 44
acgtggcttt gttgttctca tguttgacag cttatc                                         36

<210> SEQ ID NO 45
<211> LENGTH: 30
<212> TYPE: DNA
<213> ORGANISM: Artificial Sequence
<220> FEATURE:
<223> OTHER INFORMATION: Description of Combined DNA/RNA Molecule:
      Primer

<400> SEQUENCE: 45
atactctttg gccaggaccc aacgcugccc                                                30

<210> SEQ ID NO 46
<211> LENGTH: 25
<212> TYPE: DNA
<213> ORGANISM: Artificial Sequence
<220> FEATURE:
<223> OTHER INFORMATION: Description of Combined DNA/RNA Molecule:
      Primer

<400> SEQUENCE: 46
atcggcctgt cgcttgcggt autcg                                                     25

<210> SEQ ID NO 47
<211> LENGTH: 31
<212> TYPE: DNA
<213> ORGANISM: Artificial Sequence
<220> FEATURE:
<223> OTHER INFORMATION: Description of Combined DNA/RNA Molecule:
      Primer

<400> SEQUENCE: 47
acatgagaac aacaaagcca cgutgtgtct c                                              31

<210> SEQ ID NO 48
<211> LENGTH: 25
<212> TYPE: DNA
<213> ORGANISM: Artificial Sequence
<220> FEATURE:
<223> OTHER INFORMATION: Description of Combined DNA/RNA Molecule:
      Primer

<400> SEQUENCE: 48
agacgaaata cgcgatcgcu gttaa                                                     25

<210> SEQ ID NO 49
<211> LENGTH: 25
<212> TYPE: DNA
<213> ORGANISM: Artificial Sequence
<220> FEATURE:
<223> OTHER INFORMATION: Description of Combined DNA/RNA Molecule:
      Primer

<400> SEQUENCE: 49
agcgatcgcg tatttcgtcu cgctc                                                     25

```
<210> SEQ ID NO 50
<211> LENGTH: 31
<212> TYPE: DNA
<213> ORGANISM: Artificial Sequence
<220> FEATURE:
<223> OTHER INFORMATION: Description of Combined DNA/RNA Molecule:
      Primer

<400> SEQUENCE: 50
agctcctgag actcatacca ggccugaatc g                              31
```

METHOD FOR ASSEMBLY OF MULTIPLE DNA FRAGMENTS

CROSS-REFERENCE TO RELATED APPLICATIONS

The present application is a continuation of International Application No. PCT/IL98/00096, filed on Feb. 26, 1998, the disclosure of which is incorporated by reference herein.

The present invention relates to the field of genetic engineering. More particularly, the invention relates to a novel method for assembling two or more DNA fragments with high efficiency and yield.

BACKGROUND OF THE INVENTION

Building DNA constructs is the basis of genetic engineering. Manipulating recombinant DNA and its incorporation into vectors is common knowledge in the art. For example, fragments obtained by PCR techniques, may be incorporated into plasmids for cloning purposes. Generating specific DNA constructs by joining together different DNA segments, each encoding specific properties and/or possessing specific functions, is also known in the art. The state of the art has been published in a very large number of books, articles, patent applications, patents and the like, and is usually readily available and known to all of skill in the art. For example, a comprehensive account of DNA cloning procedures is provided in the three volume text by Sambrook et al. (1989) entitled "Molecular Cloning-a Laboratory Manual" 2nd edition, Cold Spring Harbor Laboratory Press. This extensive account of the prior art techniques for the combination of DNA fragments, cloning and expression thereof, is included herein by reference, in its entirety.

According to the present state of the art, the DNA fragments comprising the plasmid to be constructed are cleaved by restriction enzymes from larger entities. Next, they are connected utilizing the enzyme Ligase, which forms phosphodiester bonds between DNA fragments. Restriction enzymes cleave DNA leaving blunt or staggered ends (protruding short single stranded termini) also called overhangs. The efficiency of the ligation of blunt ended fragments is very low. Using staggered ended fragments elevates the efficiency of the ligation process, because the two fragments are being held together by the hydrogen-bonds between the complementary overhangs. Because the overhangs produced by most of the restriction enzymes are very short (2–4 bases), the connections between the complementary overhangs are weak and not very specific. Thus, when constructing a plasmid from restriction enzyme produced fragments, the yield is very low and there are many illegitimate ligations, leading to undesired products. It is therefore necessary to amplify the product usually by transfecting cells of choice such as bacterial cells, and then to identify and isolate colonies containing the DNA of choice from the ones containing undesired products. Only then can another DNA fragment be added by repetition of the whole procedure. As a result of this inefficient processes the building of complex DNA constructs is a laborious, time consuming and expensive process, in which each step necessitates the successful completion of the former. The construction of complex molecules may take several weeks to several months. Sometimes the completion of such constructs is not achieved at all. Another major drawback of the above mentioned method is that the availability of restriction site does not always coincide the construction demands. One way to overcome the above mentioned problems is to use short artificial DNA molecules called "linkers". This however further complicates the construction process, reduces the yield, increases the percentage of wrong constructs and sometimes add undesired foreign sequences.

Several methods suggest the possibility of connecting DNA fragments by producing longer complementary overhangs (8–14 nucleotides). These connections are more stable than the ones produced by restriction enzymes. In fact, they are stable enough to render the ligation step unnecessary and the bacterial cells may be transformed right after the fragments are connected. The phosphodiester bonds are generated later, by the endogenous bacterial ligation machinery.

One prior method uses single strand extensions that are created by adding nucleotides at the 3' end of a DNA strand in a template-independent fashion (Roychoudhury, R. Gene Amplif. Anal. 2:41–83, 1981). The enzyme used in this method, Terminal Transferase, incorporates nucleotides at the end of a double-stranded DNA fragment, thus creating a single-stranded tail. Since the enzyme uses the nucleotides randomly, the only way to ensure that the single-stranded tail will be complementary to a corresponding overhang created on a second DNA molecule, is to provide for each extension only one of the four nucleotides. The overhangs created with this method must therefore be homopolymeric, so that only four types of overhangs can be used, corresponding to the residues dA, dC, dG or dT. Since the overhangs created on both termini of a DNA fragment must be identical, cloning with this method is directionless and can only involve two fragments that are connected to each other at both ends, forming a circular molecule. Furthermore, the length of the overhangs cannot be specifically controlled. Finally, the method necessarily introduces an unwanted stretch of nucleotides into the final construct, the length of which cannot be determined exactly, making the method unsuitable for the purpose of cloning into expression vectors where the reading frame must be preserved.

According to another method (the commercial product "PCR-Direct™", manufactured by CLONTECH, Inc., USA) the overhangs are generated utilizing the exonuclease activity of a DNA polymerase.

U.S. Pat. No. 5,137,814 describes another method in which the overhang is generated by providing at least one dU residue instead of dT, close to the terminus of the fragment. The position of the dU residues determines the length of the overhang. This method involves an a-purination of the Uracil bases. The a-purinated residues no longer have hydrogen-bond connections with their complementary bases on the opposite strand. Moreover, they destabilize the hydrogen bonds of their neighboring bases as well. The resulting 3' protruding termini may connect to a complementary single strand sequence. A commercial product using this method is the CloneAmp® pAMP1 System (manufactured by Life Technologies Inc., USA). In the aforesaid method a 12-base overhang is used.

The use of overhangs longer than 4 nucleotides for the purpose of fragment cloning is also described in several other publications. Rashtchian et al. (Anal. Biochem. 206, p. 91–97, 1992), describe 12 nucleotide overhangs generated by Uracil DNA Glycosylase (UDG) to achieve high-efficiency cloning of single inserts into a vector. Kuijper et al. (Gene 112, p. 147–155, 1992) and Aslanidis et al. (PCR Methods Appl. 4:172–177, 1994), describe a cloning method wherein T4 polymerase is used together with a predetermined dNTP to generate overhangs of a certain length in PCR products. This method requires a specific sequence to be present in the PCR primer. Hsiao et al. (Nucleic Acids Res. 21, p. 5528–5529, 1993) and Yang et al. (Nucleic Acids Res. 21, 1889–1893, 1993) disclose generation of overhangs by the exonucleolytic activity of Exonuclease III (Exo III) or of T4 polymerase. Overhangs of 12 (Aslanidis), 8 (Yang) and 10–14 (Hsiao) nucleotides are disclosed.

The probability of producing a joint molecule composed from three molecules is the probability of joining of the first two molecules, multiplied by the probability of joining of the second and third molecules. If the joining of any two molecule is a rare event, due to the relatively short overhang, the joining of three or more molecules becomes practically useless for cloning purposes, because of the resulting low efficiency It is therefore clear that the present state of the art is not satisfactory and there is a need for an improved method by which several DNA fragments can be effectively joined together in a directional, predetermined way, in one single-step. Such a method will remove the limitations imposed on genetic engineering by the aforementioned methods, and will thus revolutionize the way in which genetic engineering is performed.

SUMMARY OF THE INVENTION

In one aspect the invention is directed to a method for assembling two or more DNA fragments with high efficiency, comprising:
 a) providing, for each DNA fragment, at least one protruding terminus, or "overhang", capable of hydrogen bonding to a complementary sequence on at least one strand of a second DNA fragment, said overhang having at least 15 bases; and
 b) mixing two or more said DNA fragments under conditions suitable to promote joining thereof.

The method of the invention is based on the very surprising finding that increasing the number of bases in complementary overhang from 12 to at least 15, permits to reduce the ratio of the reagents from about 1:100–300 to about 1:1. At the same time, this permits to join multiple fragments (3 or more), because of the high efficiency of the process.

According to one embodiment of the invention three or more fragments are joined by the method of the invention, and the molar ratio of each DNA pairs is about 1:1 to 1:50.

The present invention provides a DNA fragment comprising an overhang of at least 15 nucleotides or an end portion suitable to be converted into such an overhang. The invention further provides said DNA fragment, for use in the above method of the invention.

According to another preferred embodiment of the invention, the number of bases in the overhang is between 20 and 30. While, as stated above, the improvement of the process efficacy is very dramatic when passing from 12 to 15 bases, there is still a further steep improvement in the efficacy, when increasing the number of bases to about 20. This increase reaches a plateau above 20 bases. Taking into account that, when joining a number of fragments, the overall efficiency of the process decreases, it is of course desirable to employ the lowest number of bases in the overhang which still provides for increased joining efficiency. As stated, in most cases this optimal length will be in the neighborhood of 20 bases.

As will be appreciated by the skilled person, this is most surprising because such a dramatic increase in binding ability of fragments (from almost no binding when overhangs are 12 bases long to almost 100% binding when the overhangs are 21 bases long) was unexpectable. Although some improvement could have been expected by increasing the length of the overhang, such a dramatic improvement (two orders of magnitude) was entirely surprising. The art, in fact, has continued to use stepwise cloning techniques, with all the inherent disadvantages, and has not attempted in practice to use overhangs longer than 12 bases.

BRIEF DESCRIPTION OF THE DRAWINGS

FIG. 1 is plasmid pGS101. There is an overlap of 12 bp between every two fragments which are joined together. The plasmid is assembled from three fragments.

FIG. 2 is plasmid pGS102. There is an overlap of 12 bp between every two fragments which are joined together. The plasmid is assembled from four fragments.

FIG. 3 is plasmid pGS103. There is an overlap of 12 bp between every two fragments which are joined together. The plasmid is assembled from four fragments.

FIG. 4 is plasmid pGS201. There is an overlap of 20–21 bp between every two fragments which are joined together. The plasmid is assembled from three fragments.

FIG. 5 is plasmid pGS202. There is an overlap of 20–21 bp between every two fragments which are joined together. The plasmid is assembled from four fragments.

FIG. 6 is plasmid pGS203. There is an overlap of 20–21 bp between every two fragments which are joined together. The plasmid is assembled from four fragments.

FIG. 7 shows the results obtained by an Agarose gel run, to check fusion ability of identical fragments with different overhang lengths.

FIGS. 8 A, B, C, D, E, F, and G correspond to plasmids pGS101, pGS201, pGS102, pGS202, pGS103 and pGS203, respectively. The plating was carried out on selective plates that would minimize background noise as explained in the text.

FIG. 9 illustrates the constructs made in Example 3, along with the number of transformants obtained;

FIG. 12 shows a construct made by joining 3 different fragments using exonuclease III-created overhangs in the experiment of example 4;

DETAILED DESCRIPTION OF THE INVENTION

General Procedures

Overview

Figure 1:
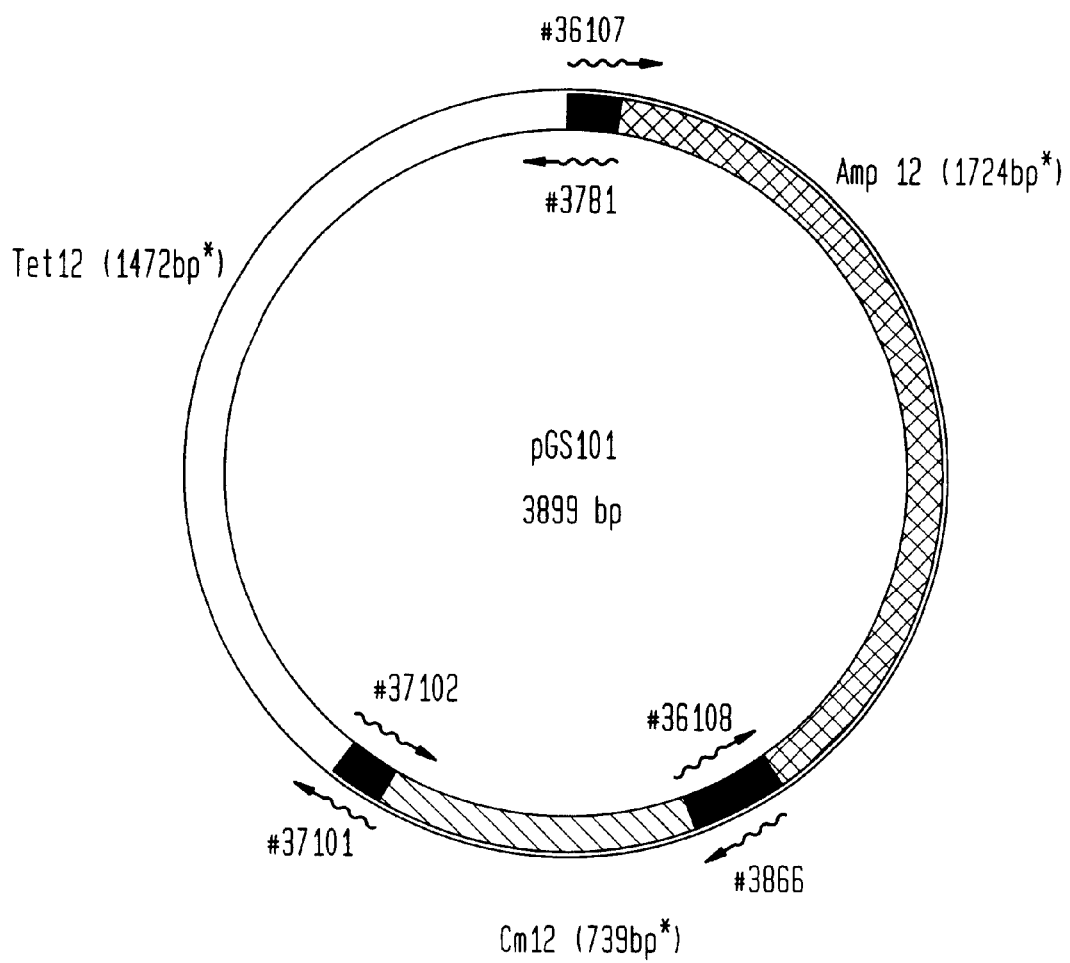
FIGS. 1–6 illustrate plasmids produced in Example 3. In the FIGS. 1–6, the dark, cross-hatched bar depicts the fragment amplified from pBR322 which carries the $Amp^r$ gene and the origin of replication. The empty bar depicts the fragment PCR amplified from pBR322 which carries the $Tet^r$ gene. The hatched bar depicts the PCR amplified fragment from pACYC184 which carries the $Cm^r$ gene. The arrows mark primers, where the arrow head is the 3' end of the primer, and the wavy tails mark the various repetitive sequences at the 5' end of the primers. The primer's number is given above or below the arrow. The black area denotes repetitive sequences situated at the connection between two fragments.

The present invention is based on the surprising discovery that by increasing the length of complementary overhangs of two DNA fragments from 12 bases, as in the prior art, to 15 bases or more, the tendency of the fragments to be connected to each other rises, steeply increasing, from close to 0% when 12 base overhangs are used, to almost 100% when around 20 bases are employed. When long complementary overhangs of 15 bases or more are used, a large number of DNA fragments can be assembled in a single step in a predetermined, directional manner. In addition, when connections between just two fragments are made, the yield of cloned products is much higher than that of the prior art, when operating according to the invention.

A number of procedures can be used in order to create these overhangs. In the examples detailed below, three different procedures were used.

The First Procedure

The first procedure is used in examples 1–3. Examples 1 and 2 illustrate the difference in the connecting ability of fragments with complementary overhangs of different lengths in-vitro by subjecting the connected fragments to agarose gel analysis. In the third example, successful cloning of a plasmid assembled from five fragments using the procedure was demonstrated. The fragments were connected to each other in-vitro, and then transformed into bacterial cells.

The procedure is as follows:

The fragments which are to be attached to each other in a directional fashion are preferably prepared by utilizing the well-established Polymerase Chain Reaction (PCR). This provides suitable amounts of the fragments and is especially preferred when the fragments to be used are originally obtained or available only in small amounts, for example from restriction-endonuclease treated plasmid DNA, genomic DNA, or cDNA libraries in which the desired fragments are present in small amounts. In this way, the original fragments are greatly amplified and by virtue of the use of pre-selected specific primers, the ends of the PCR-amplified fragments will contain the desired pre-selected complementary sequences.

The primers are designed such that they consist of two regions: A 3' region that is complementary to the template and a 5' region that contains a sequence complementary to a sequence at the 5' end of the fragment it is designed to join. In this 5' region, several dT residues are substituted by dU residues. During PCR, the thermostable DNA Polymerase does not distinguish between the dT and dU residues and incorporates dA opposite both of these residues in the newly synthesized strand.

Following PCR, the fragments are mixed together and the enzyme Uracyl DNA Glycosylase (UDG) is added to the reaction mixture. UDG specifically attacks the dU bases and a-purinates them. The a-purinated residues no longer have hydrogen bonds with their complementary bases. Furthermore, they destabilize the hydrogen bonds of their neighboring bases as well. As a result, the double stranded structure near the terminus falls apart. Two open strands are created at the end of the segment: 1. A 5' single strand with several a-purinated residues that can no longer form hydrogen bonds with a complementary strand. 2. A 3' single strand with no a-purinated residues that can form such bonds. Although this single strand is not, strictly speaking, an overhang, it is equivalent to it and behaves as such for all practical purposes. The complementary regions of DNA generated in this procedure are made of repetitive sequences. Therefore, it can be used to illustrate that the length of the exposed ends is the key parameter in determining the tendency of fragments to be connected to one other: The difference between the constructs in the various experiments is in the lengths of the repetitive complementary regions and not in the sequence.

Two fragments that have such complementary single strands can form hydrogen-bond connections with each other. If such fragments are used to transform bacterial cells, their 5' a-purinated single strands are degraded by cellular enzymes. Furthermore, endogenous ligases convert the joint fragments into a single DNA molecule. Details of the procedure are described in Examples 1–3 below.

The Second Procedure

In Example 4, a second procedure was used. This procedure uses the enzyme Exonuclease III (herein after ExoIII) to generate the overhangs. Other enzymes having an exonuclease activity such as T4 DNA polymerase or T7 DNA polymerase may be used as well. In addition to the above mentioned enzymes which have 3'→5' exonuclease activity, enzymes with 5'→3' exonuclease activity may also be used, depending on the circumstances. Procedures similar to this one are disclosed in the above Hsiao et al. and Yang et al. The specific procedure is elaborated in a copending application of the same applicant herein (filed on the same day as this application, and identified as Attorney Docket 4190/96, Israeli Patent Application No. 120378). The procedure can be applied for the joining of PCR fragments as in examples 1–3 as well as for the joining of a mixture of DNA fragments that are generated by restriction enzyme cleavage together with PCR generated fragments. In example 4 the fragments were produced by PCR to generate a plasmid assembled from three segments.

The procedure is as follows:

The terminal portions of the fragments that are to be joined have to be complementary to each other. This can be achieved by producing the PCR fragments in the following way: The primers of a first DNA fragment that is to be PCR produced and is to be joined to a second and to a third fragment should be synthesized having two regions: 1. A 3' region that is complementary to the template. 2. A 5' region that is complementary to the terminal portion of the fragment that is to be joined to the first fragment. The length of the complementary regions should be 15 nucleotides (nt) or more.

The various DNA fragments to be joined are mixed together and an exonuclease enzyme is added to the mixture. In the case of example 4, ExoIII was used. ExoIII is an exonuclease that catalyzes the stepwise removal of mononucleotides from 3' hydroxyl termini of double stranded DNA. It is added in access and the reaction is incubated at 60° C. to ensure slow digestion. The reaction is allowed to proceed for a time sufficient to digest the ends of the fragments, exposing 5' overhangs. These overhangs usually consist of a region which is longer than the complementary portion.

Once the reaction is stopped, the temperature is raised to 75° C. The reaction mixture is then cooled slowly. This facilitates the joining of complementary overhangs while minimizing illegitimate connections. Following the cooling, dNTPs and T7 DNA Polymerase are added in order to fill any gaps that may have been formed due to ExoIII overdigestion. At this stage, the mixture is used to transform bacterial cells. Further elaboration of the procedure is given in Example 4 below.

The Third Procedure

In example 5 a third procedure was used. This procedure is similar, in many respects to the first one but has the advantage that the junctions between the various fragments require no addition of linker nucleotides. An elaborated description of this procedure is disclosed in a copending application (filed on the same day as this application, and identified as Attorney Docket 4149196, Israeli Patent Application No. 120377). As will be demonstrated below, a single dU residue near the termini of the fragments, along with UDG and the reagent N,N dimethylethylenediamine were employed in this procedure to generate seamless connections between fragments. In example 5, the cloning of a plasmid assembled from eight separate segments is demonstrated. To date, this is the only disclosure of an assembly of a plasmid from so many segments in a single step.

The procedure is as follows:

This procedure allows the formation of true 3' overhangs using a single dU residue in each of the primers to be connected. It is based on the ability to chemically create a nick at the 3' end of an a-purinated dU residue.

The fragments are produced by PCR. As in the other examples, the terminal portions of the fragments that are to be joined have to be complementary to each other. As described in example 5, this is achieved by producing the PCR fragments in the following way: The primers of a DNA fragment that is to be PCR produced and is to be connected to two other fragments are synthesized having two regions: 1. A 3' region that is complementary to the template. 2. A 5' region that is complementary to the terminal portion of the fragment that is to be joined to the said fragment. The length of the complementary regions should be 15 nt or more. In each primer, a dT residue is substituted by a dU residue at the junction between the complementary and non complementary regions.

The various DNA fragments to be joined are mixed together and UDG, as well as N,N dimethylethylenediamine are added to the mixture. The enzyme a-purinates the dU base and the chemical generates a nick at the 3' side of the a-purinated residue.

Following the creation of the above mentioned nicks, the temperature is raised to 70° C. in order to disconnect the short single-strand stretch 5' of the a-purinated dU residues from the rest of the fragment. Thus, 3' overhangs which constitute the complementary regions are created. After removing the nicked oligonucleotides, the reaction is cooled slowly to allow joining between the complementary overhangs while minimizing illegitimate connections. Following the cooling, the mixtures are used to transform bacterial cells. Further elaboration of the procedure is found in Example 5 below.

The examples to follow are provided for the purpose of illustration only, and it is clear that the invention is not limited to any particular method or procedure for creating the aforesaid overhangs.

EXAMPLE 1

In Vitro Hybridization of Fragments with Complementary Overhangs of Different Lengths Overview In order to demonstrate the superiority of connection between DNA fragments having long overhangs, the degree of inter-connection of fragments with different lengths of overhangs was tested. Five pairs of fragments, each containing different length of the complementary region, were produced by PCR. Each pair consisted of 1). A fragment of about 1400 bp designated Tet, which was PCR amplified from the $Tet^r$ gene (conferring resistance to tetracyclin) of pBR 322. 2). A fragment of about 1700 bp designated Amp, which was PCR amplified from the $Amp^r$ gene (conferring resistance to ampicillin) of pBR322. One of the two primers that was used to amplify the Tet fragment in each pair contained, in addition to a region which was complementary to the template DNA, a 5' tail with repeats of three bases CUA. Likewise, one of the primers used for Amp amplification contained a 5' tail with repeats of UAG. Note, that CUA and UAG are complementary to one another. In the first pair, the tail consisted of four repeats (12 bases) and the tails of the second, third, fourth and fifth pairs consisted of five, six, seven and ten repeats respectively (15, 18, 21 and 30 bases).

The Amp fragment and the Tet fragment of each pair were mixed, and their 3' overhang exposed utilizing UDG. After an annealing time period the mixtures were subjected to agarose gel analysis (FIG. 7).

Primers and PCR Conditions

For each of the 5 reactions, two fragments were produced. An $Amp^r$ fragment and a $Tet^r$ fragment. The only variable between the five $Amp^r$ fragments (or between the five Tet fragments) was the length, but not the sequence, of the complementary region. The hybridization rate between pairs of DNA fragments was tested.

A) The Primers and Production of the Fragments

In each of the primers below, and in the following examples, the * symbol is written below the dU residue in order to emphasize it. All of the primer sequences given herein are written in 5' to 3' direction.

```
                                      Tet sense primer
Primer SEQ. ID NO. 1
(also designated 31160) - upstream of Tet (PBR322: 1-22)
--irrelevant tail-     22nt
 AGCTCCTGA-TTCTCATGTTTGACAGCTTATC
```

```
                                      Tet antisense primers
note: the 5 primers below differ from one another only by the
number of CUA repeats at their 5' end.

Primer SEQ. ID NO. 2
(also designated 3781) - downstream of Tet (pBR322: 1449-1425)
                          25nt
---12nt (CUA)x4--- TGG CCA GGA CCC AAC GCT GCC CGA G
       *
```

-continued

Primer SEQ. ID NO. 3
(also designated 4082) - downstream of Tet (pBR322: 1449—1425)
                              25nt
---15nt (CUA)x5--- TGG CCA GGA CCC AAC GCT GCC CGA G
         *

Primer SEQ. ID NO. 4
(also designated 4353) - downstream of Tet (pBR322: 1449—1425)
                              25nt
---18nt (CUA)x6--- TGG CCA GGA CCC AAC GCT GCC CGA G
         *

Primer SEQ. ID NO. 5
(also designated 4635) - downstream of Tet (pBR322: 1449—1425)
                              25nt
---21nt (CUA)x7--- TGG CCA GGA CCC AAC GCT GCC CGA G
         *

Primer SEQ. ID NO. 6
(also designated 5535) - downstream of Tet (pBR322: 1449—1425)
                              25nt
---30nt (CUA)x10--- TGG CCA GGA CCC AAC GCT GCC CGA G
         *
(Note that primers SEQ. ID NO. 2—6 are homologously complementary to primers SEQ. ID NO. 8—12 respectively at their
5' ends)

Amp sense primer
                         _____

Primer SEQ. ID NO. 7
(also designated 4142) - downstream of Amp (pBR322 2460—2479)
---irrelevant tail---       20nt:
ATTGGTGCCCTTAAACGCCTG-AACGCAGGAAAGAACATGTG Amp antisense primers
                         _____ note: the 5 primers below differ from one another only by the
number of UAQ repeats at their 5' end.

Primer SEQ. ID NO. 8
(also designated 36107) - upstream of Amp (pBR322: 4136—4159)
                              24nt
---12nt (UAG)x4---AAG AGT ATG AGT ATT CAA CAT TTC
         *

Primer SEQ. ID NO. 9
(also designated 3993) - upstream of Amp (pBR322: 4136—4159)
                              24nt
---15nt (UAG)x5---AAG AGT ATG AGT ATT CAA CAT TTC
         *

Primer SEQ. ID NQ. 10
(also designated 4270) - upstream of Amp (pBR322: 4136—4159)
                              24nt
---18nt (UAG)x6---AAG AGT ATG AGT ATT CAA CAT TTC
         *

Primer SEQ. ID NO. 11
(also designated 4560) - upstream of Amp (pBR322: 4136—4159)
                              24nt
--21nt (UAG)x7---AAG AGT ATG AGT ATT CAA CAT TTC
         *

Primer SEQ. ID NO. 12
(also designated 5434) - upstream of Amp (pBR322: 4136—4159)
                              24nt
---30nt (UAG)x10---AAG AGT ATG AGT ATT CAA CAT TTC
         *
Note that the primers SEQ. ID NO 8—12 are homogously complementary to primers SEQ. ID NO. 2—6 respectively at their 5'ends.

Note that primers SEQ. ID NO. 8–12 are homologously complementary to primers SEQ. ID NO. 2–6 respectively at their 5' ends.

The template for the PCR reaction was pBR 322 DNA. The full sequence and maps of the various regions of this plasmid is well known and can be accessed from GenBank database under accession no. J01749 (pBR322).

The various fragments were produced by PCR, as follows:

PCR of Tet Fragments (the number at the right denotes the length of the overhang)

|  | Tet 12 | Tet 15 | Tet 18 | Tet 21 | Tet 30 |
|---|---|---|---|---|---|
| 10 μl (0.1 μg/μl) | SEQ ID 2 | SEQ ID 3 | SEQ ID 4 | SEQ ID 5 | SEQ ID 6 |
| 10 μl (0.1 μg/μl) | SEQ ID 1 | SEQ ID 1 | SEQ ID 1 | SEQ ID 1 | SEQ ID 1 |
| pBR322 DNA | 40 ng | 40 ng | 40 ng | 40 ng | 40 ng |
| 180 μl PCR mix in each tube | | | | | |

PCR of Amp Fragments (the number at the right denotes the length of the overhang)

|  | Amp 12 | Amp 15 | Amp 18 | Amp 21 | Amp 30 |
|---|---|---|---|---|---|
| 10 μl (0.1 μg/μl) | SEQ ID 8 | SEQ ID 9 | SEQ ID 10 | SEQ ID 11 | SEQ ID 12 |
| 10 μl (0.1 μg/μl) | SEQ ID 7 | SEQ ID 7 | SEQ ID 7 | SEQ ID 7 | SEQ ID 7 |
| pBR322 DNA | 40 ng | 40 ng | 40 ng | 40 ng | 40 ng |
| 180 μl PCR mix in each tube | | | | | |

PCR mix:

| dNTPs (2.5 mM each) | 128 μl |
|---|---|
| Buff x10 | 16 μl |
| H$_2$O | 1088 μl |
| TaQ DNA Polymerase 5 U/μl | 6.4 μl |

Temperature regime
94° C. 40 sec
40° C. 2 min
72° C. 4 min
30 cycles
72° C. 5 min
6° C. infinitely All the required fragments were obtained. The concentration of each fragment was determined by measuring the density of the band created by each DNA fragment on an agarose gel. The volumes used for the following experiment were corrected accordingly.

B) Checking Fusion Ability

Each pair of fragments having the same length of repeats was put in a different Eppendorf tube. The DNA was incubated at 37° C. with UDG in order to create the overhangs and allow hybridization (see details below). The products of the reaction were subjected to electrophoresis on an agarose gel at 60V for 60 min, stained with ethidium bromide and photographed under U.V. light (FIG. 7). Amp fragments are 1.7 kb in length, Tet fragments are 1.4 kb, and fragments of Amp+Tet that have hybridized to each other are 3.1 kb in length. The difference in the density between the Amp band, the Tet band and the Amp+Tet band, reflect the ability of the fragments to adhere to each other. Comparisons could thus be made between the adherence abilities of fragment-pairs having different overhang-lengths.

The Amp and Tet fragments (of each pair) were mixed together as follows (The number of the mix is equivalent to the number of the complementary overhang).

| Mix | 12 | 15 | 18 | 21 | 30 |
|---|---|---|---|---|---|
| Amp frag. | 3 μl | 1.5 μl | 1 μl | 1 μl | 1 μl |
| Tet frag. | 3 μl | 2 μl | 2.5 μl | 1.5 μl | 5 μl |
| H$_2$O | 2 μl | 4.5 μl | 4.5 μl | 5.5 μl | 2 μl |
| UDG Buff.x10 | 1 μl | 1 μl | 1 μl | 1 μl | 1 μl |

UDG Buff.x10 = 200 mM Tris HCl pH 8.4, 500 mM KCl, 15 mM MgCl$_2$

The content of each of the tubes was divided into two. In the first tube, 0.54 μl UDG was added. In the second, 0.54 μl H$_2$O was added as a blank control. The tubes were incubated at 37° C. for 5 hours. Then, the content of the tubes was transferred into an 0.8% TAE Agarose gel. The gel was run at 60V for 60 min, stained with ethidium bromide and photographed under U.V. light. Results are shown in FIG. 7.

| OVERHANG | 12 | | 15 | | 18 | | 21 | | 30 | |
|---|---|---|---|---|---|---|---|---|---|---|
| Tube No. | 1 | 2 | 3 | 4 | 5 | 6 | 7 | 8 | 9 | 10 |
|  | UDG | H$_2$O | UDG | H$_2$O | UDG | H$_2$O | UDG | H$_2$O | UDG | H$_2$O |
| Lane on the gel: | 1 | 2 | 3 | 4 | 5 | 6 | 7 | 8 | 9 | 10 |

The experiment shows: 1) Almost no fusion is observed when the overhangs are 12 bp long. 2) In lane 7, there are more Tet fragments then Amp fragments. Therefore, even though there are almost no free Amp fragments left, some free Tet fragments still exist. 3) Both in lanes 7 and 9, there are no free Amp fragments left. There is an outstanding ability of overhangs of 21 and 30 bp to adhere to one another.

In conclusion, the results of the experiment indicate that:

1) Almost no fusion is observed when the overhangs are 12 bp long.

2) There is a dramatic increase in adherence starting with overhangs 15 bases long.
3) There is an outstanding ability of almost 100% of overhangs of 21 and 30 bases to adhere to one another.

EXAMPLE 2

Figure 11:
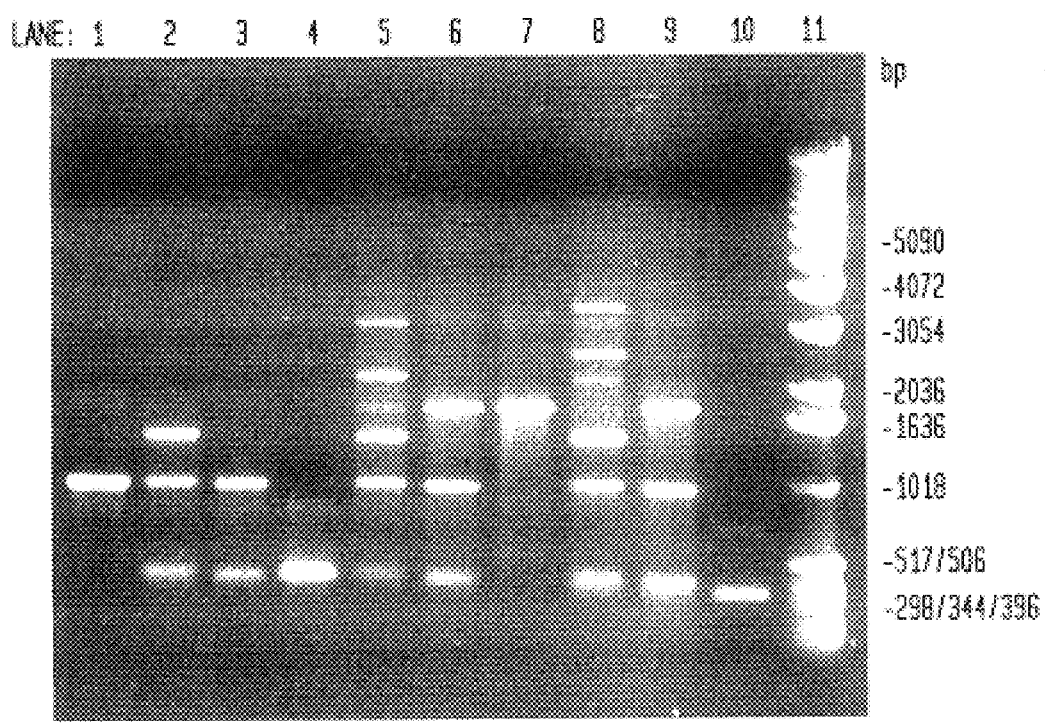
FIG. 11 shows the results of gel runs of the products obtained in Example 2.

Multi DNA Fragment Assembly (MDFA) in-vitro:
Comparison between fragments with overhangs of 12 and 20–21 bases I. Overview:

The following experiment was carried out in order to show the stronger affinity and higher stability of connection between fragments with overhangs of 21 bases versus the connection of fragments having overhangs of 12 bases. Two sets of fragments were generated by PCR. In the first set, the length of the complementary regions at each end of the fragments was 12 bp. In the second set, the length was 20–21 bp. The complementary regions were repeats of 3 or 5 bases. Therefore, the sequence of the complementary regions in analogous fragments of the two sets can be regarded as identical, the only difference being the overall length of the repeated region. Four different fragments of each set were generated by PCR, mixed together and 3' complementary overhangs were exposed utilizing UDG. After an annealing time period, they were run on agarose gel in order to check the degree of the connection between the fragments (FIG. 11).

II. Primers and PCR Conditions:

Four unique fragments of each set (one set with 12 bp complementary sequences and the other set with 21 bp complementary sequences) were amplified by PCR. The fragments were designated TetA, TetB, Amp, and CmB.

TetA was PCR amplified from pBR322 (bases 1–937).

TetB was PCR amplified from pBR322 (bases 1067–1449).

Amp was PCR amplified from pBR322 (bases 2460–4159).

CmB was PCR amplified from pACYC184 (bases 3768–4086).

The fragments were designed to connect with each other in the following order: TetA-TetB-Amp-CmB. The primers were synthesized with 3' ends that would enable making PCR fragments from pBR322 and pACYC184 templates as in the former experiments. Two sets of 8 primers were synthesized. In each set, three junctions with complementary repeats were designed. A junction between the TetA and the TetB fragments, a junction between the TetB and the Amp fragments and a junction between the Amp and the CmB fragments. Each of the repeats in a set was different and was complementary-homologous only to one of the other repeats. The PCR fragments that were produced could therefore be connected to one another via the repeats, to form a linear fusion product.

Primers of the First Set: Primers Containing Repeats or Near-repeats of 12 Nucleotides with dUs at their 3' Ends

```
Primer SEQ ID NO. 13 - Tet A sense
(also designate4 37101)     upstream of Tet (pBR322: 1-25)
            ----12nt------              25nt
            AU CAUAU CAUAU TTC TCA TGT TTG ACA GCT TAT CAT C
            *  * *    * *

Primer SEQ ID NO. 15 - Tet A antisense
(also designated 37103)
            ----12nt------         25nt   (pBR322: 913-937)
            UA CUAUA CUAUA CAT GCC GGC GAT AAT GGC CTG CTT C
            *  * *    * *

Primer SEQ ID NO. 16 - Tet B sense
(also designated 37104)
            -----12nt-----         25nt  (pBR322: 1067-1091)
            UAUAG UAUAG UA GTA GAT GAC GAC CAT CAG GGA CAG C
            *  *    * *   *

Primer SEQ ID NO. 2 Tet B antisense
downstream of Tet (pBR322: 1449-1425)
            ---12nt CUAx4--              25nt
            CUA CUA CUA CUA TGG CCA GGA CCC AAC GCT GCC CGA G
             *    *    *    *

Primer SEQ ID NO. 8 - Amp sense
            upstream of Amp (pBR 322: 4159-4136)
--12 nt UAGx4 -         24 nt
UAG UAG UAG UAG AAG AGT ATG AGT ATT CAA CAT TTC
 *    *    *    *

Primer SEQ ID NO. 18 - antisense Amp
(also designated 36108)
                              downstream of ORI
---12 nt AUGx4-       pBR322 (2460-2483)
AUG AUG AUG AUG AAC GCA GGA AAG AAC ATG TGA GCA
 *    *    *    *

Primer SEQ ID NO. 17 - Cm B sense
(also designated 37106)
            ----12nt------       25nt (pACYC184: 4086-4062)
            AU CUAAU CUAAU TAC GGT GAA AAC CTG GCC TAT TTC C
            *  * *    * *
```

-continued

Primer SEQ ID. NO. 14 - Cm B antisense
(also designated 3866)
```
          ---12nt CAUx4--          26nt (pACYC184: 3768-3793)
          CAU CAU CAU CAU CAG GCG TTT AAG GGC ACC AAT AAC TG
           *   *   *   *
```

PCR Reactions
(The number on the right denotes the length of the overhang)

| reaction | Tet A12 | Tet B12 | Amp12 | Cm B12 |
|---|---|---|---|---|
| 20 ml primer 1 | SEQ ID 13 | SEQ ID 16 | SEQ ID 18 | SEQ ID 14 |
| 20 ml primer 2 | SEQ ID 15 | SEQ ID 2 | SEQ ID 8 | SEQ ID 17 |
| (Primer concentration: 0.1 µg/µl) | | | | |
| expected fragment size: | 961 bp | 406 bp | 1724 bp | 340 bp |
| mix | | | | |
| 2 µl dNTP's (2.5 mM each) | | 112 µl | | |
| 2.5 µl 10 × Buff. | | 140 µl | | |
| 18 µl H2O | | 1008 µl | | |
| 0.1 µl Taq (5 u/µl) | | 5.6 µl | | |
| put 360 µl mix in each tube. add primers | | | | |
| add 1 µl DNA | pBR322 | pBR322 | pACYC184 | pBR322 |

(DNA concentration: 40 ng/µl)

Temperature regime

94° C. 40 sec
40° C. 2 min
72° C. 4min 30 cycles
72° C. 5 min
6° C. infinitely

Primers of the Second Set: Primers Containing Repeats of 21 Nucleotides with dUs at their 3' Ends

```
Primer SEQ. ID NO. 19 - TetA sense
(also designated 4554)       - upstream of Tet (pBR322: 1-25)
-----20nt CAUAUx4------              25nt
CAUAU CAUAU CAUAU CAUAU CAUAU TTC TCA TGT TTG ACA GCT TAT CAT C
  * *   * *   * *   * *   * *

Primer SEQ. ID NO. 21 - TetA antisense
(also designated 4558)       - (pBR322: 913-937)
-----20nt CUAUAx4----              25nt
CUAUA CUAUA CUAUA CUAUA CAT GCC GGC GAT AAT GGC CTG CTT C
  * *   * *   * *   * *

Primer SEQ. ID NO. 22 - TetB sense
(also designated 4559)       - (pBR322: 1067-1091)
-----20nt UAUAGx4------              25nt
UAUAG UAUAG UAUAG UAUAG GTA GAT GAC GAC CAT CAG GGA CAG C
 * *   * *   * *   * *

Primer SEQ. ID NO. 5 - TetB antisense
                             downstream of Tet (pBR322: 1449-1425)
------21nt CUAx7----------              25nt
CUA CUA CUA CUA CUA CUA CUA TGG CCA GGA CCC AAC GCT GCC CGA G
 *   *   *   *   *   *   *

Primer SEQ. ID NO. 11 - Amp sense
                                  -pBR322 (4159-4136)
-----21nt UAGx7----------              24nt
UAG UAG UAG UAG UAG UAG UAG AAG AGT ATG AGT ATT CAA CAT TTC
 *   *   *   *   *   *   *

Primer SEQ. ID NO. 24 Amp antisense
(also designated 4561)       -pBR322 coding (2460-2483)
------21nt AUGx7----------              24 nt
AUG AUG AUG AUG AUG AUG AUG AAC GCA GGA AAG AAC ATG TGA GCA
 *   *   *   *   *   *   *
```

-continued

```
Primer SEQ. ID NO. 23 - Cm B sense
(also designated 4556)        -(pACYC184: 4086-4062)
-----20nt CUAAUx4------             25nt
CUAAU CUAAU CUAAU CUAAU TAC GGT GAA AAC CTG GCC TAT TTC C
 *     *     *     *    *   *   *   *   *   *   *   *

Primer SEQ. ID NO. 20 - CmB antisense
(also designated 4743)        -(pACYC184: 3768-3793)
-------21nt CAUx7---------            26nt
CAU CAU CAU CAU CAU CAU CAU CAG GCG TTT AAG GGC ACC AAT AAC TG
 *   *   *   *   *   *   *
```

PCR Reactions

| reaction | Tet A21 | Tet B21 | Amp21 | Cm B21 |
|---|---|---|---|---|
| 20 μl primer 1 | Seq. ID 19 | Seq. ID 22 | Seq. ID 11 | Seq. ID 20 |
| 20 μl primer 2 (primer concentration: 0.1 μg/μl) | Seq. ID 21 | Seq. ID 5 | Seq. ID 24 | Seq. ID 23 |
| expected fragment size: | 977 bp | 423 bp | 1742 bp | 357 bp |
| mix | | | | x128 |
| 2 μl dNTP's (2.5 mM each) | | | | 256 μl |
| 2.5 μl 10xBuff. | | | | 320 μl |
| 18 μl H2O | | | | 2304 μl |
| 0.1 μl Taq 5 U/μl (dNTP concentration 2.5 mM each) | | | | 12.8 μl |

-continued

| put 360 ml mix in each tube. add primers | | | | |
|---|---|---|---|---|
| add 1 μl DNA (DNA concentration: 40 ng/μl) | pBR322 | pBR322 | pACYC184 | pBR322 |

Temperature regime
94° C. 40 sec
40° C. 2 min
72° C. 4 min
30 cycles
72° C. 5 min
6° C. infinitely III. Fusion of the Fragments After the amplification, the fragments were mixed and 3' complementary overhangs were exposed utilizing UDG. Fusions of either 2 fragments, 3 fragments or 4 fragments of the two sets (i.e., of fragments that were created with primers of the two above-described sets) were performed. After the fusion the reactions were run on a 0.8% agarose gel in 1× TAE stained with ethidium bromide and photographed under U.V. light (FIG. 11).

In order to demonstrate the size of the various fragments, they were run in separate lanes (TetA, TetB, Amp, and CmB, in lanes 1, 4, 7, and 10 respectively). Only fragments of the first set were run, since those of the second set have identical lengths. The various mixtures that included the fused fragments were also run.

Reactions and lanes no. on the gel:

1. 1.8 μl Tet A12
2. 1.8 μl Tet A21 — 1.8 μl Tet B21 — 13.6 μl H₂O — 2 μl UDG Buff × 10 — 0.8 μl UDG
3. 1.8 μl Tet A12 — 1.8 μl Tet B12 — 13.6 μl H₂O — 2 μl UDG Buff × 10 — 0.8 μl UDG
4. 1.8 μl Tet B12
5. 1.8 μl Tet A21 — 1.8 μl Tet B21 — 1.8 μl Amp 21 — 11.8 μl H₂O — 2 μl UDG Buff × 10 — 0.8 μl UDG
6. 1.8 μl Tet A12 — 1.8 μl Tet B12 — 1.8 μl Amp 12 — 11.8 μl H₂O — 2 μl UDG Buff × 10 — 0.8 μl UDG
7. 1.8 μl Amp 12
8. 1.8 μl Tet A21 — 1.8 μl Tet B21 — 1.8 μl Amp 21 — 1.8 μl Cm B21 — 10 μl H₂O — 2 μl UDG Buff × 10 — 0.8 μl UDG
9. 1.8 μl Tet A12 — 1.8 μl Tet B12 — 1.8 μl Amp 12 — 1.8 μl Cm B12 — 10 μl H₂O — 2 μl UDG Buff × 10 — 0.8 μl UDG
10. 1.8 μl Cm B12
11. Molecular Weight Markers the concentration of all the DNA fragments was 0.09 pmol/μl. UDG Buff.x10=200 mM Tris HCl pH 8.4, 500 mM KCl, 15 mM MgCl₂

The reactions were incubated at 37° C. for 5 hours and then run on a gel. The results are shown in FIG. 11. The order of the lanes is shown at the top, and the sizes of the molecular weight markers are indicated at the right side of the photograph.

From the above results, the following conclusions can be drawn:

1. Detectable fusion products are observed when the overhangs are 21 bp long, but not when they are 12 bp long.
2. Since the fusion efficiency of 21 bp overhangs is high but less then 100%, products of partial fusions are also observed. In lanes 2, 5 and 8, the band which appears highest on the gel, has the length of the required end product.
3. The results demonstrate that the amount of the required product decreases when the number of fragments required to generate it, increases.

This example clearly demonstrated the advantage of using fragments with long overhangs. No end products were observed when using fragments with 12 nt overhangs. When using fragments with 20–21 nt overhangs, the fusion of 2–3 and 4 fragments is clearly demonstrated.

EXAMPLE 3

Multi DNA Fragment Assembly (MDFA) in-vivo: Comparison between Fragments with Overhangs of 12 and 20–21 Bases The following experiment illustrates the advantage of connecting fragments having 20–21 base overhangs as compared to fragments having 12 base overhangs, iLn vivo. Fragments having either 12 base overhangs or 20–21 base overhangs were produced by PCR and connected, forming circular plasmids. These plasmids were transformed into bacterial cells and the colonies were examined.

Figure 2:
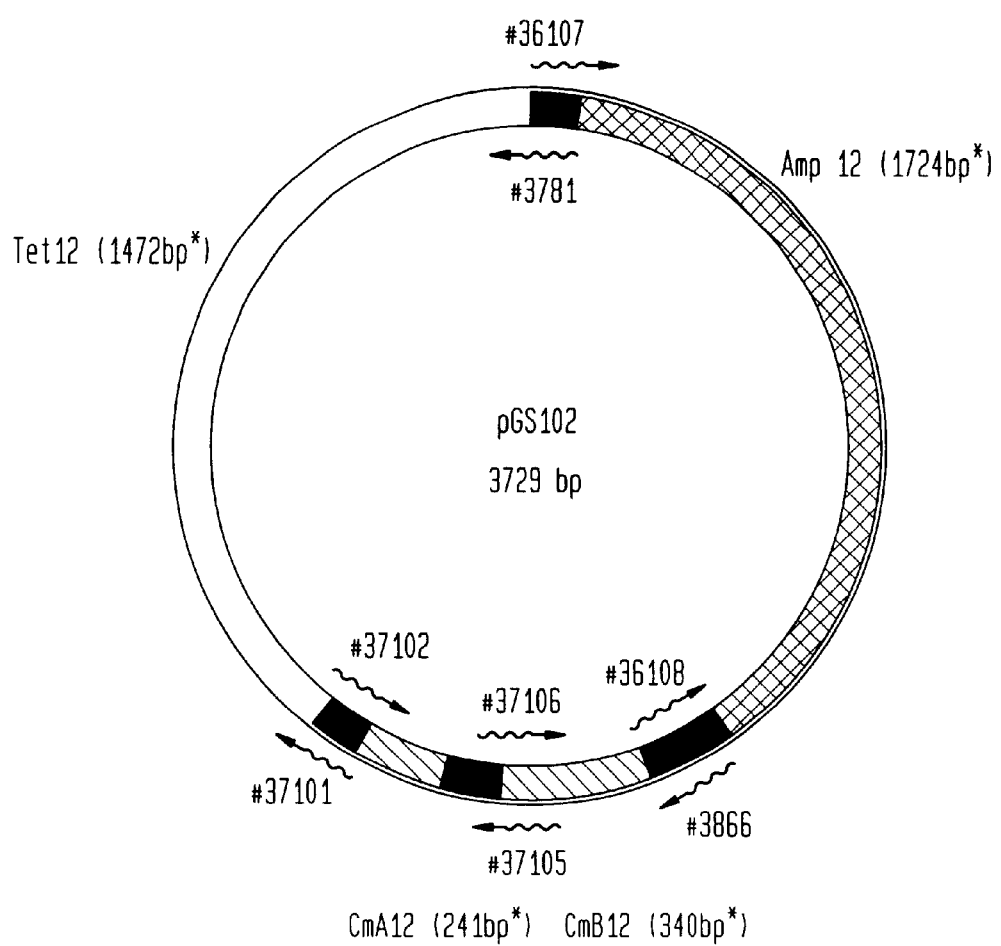
Figure 3:
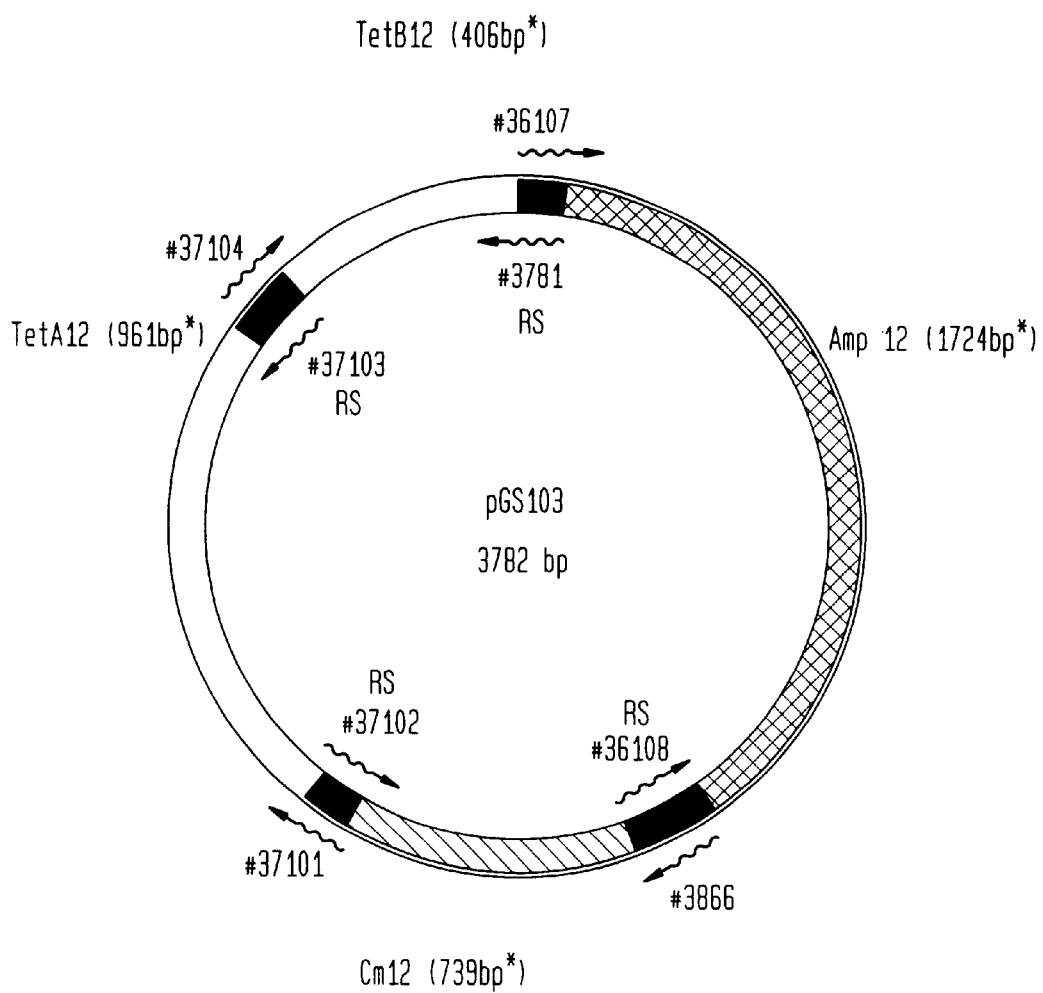
Figure 4:
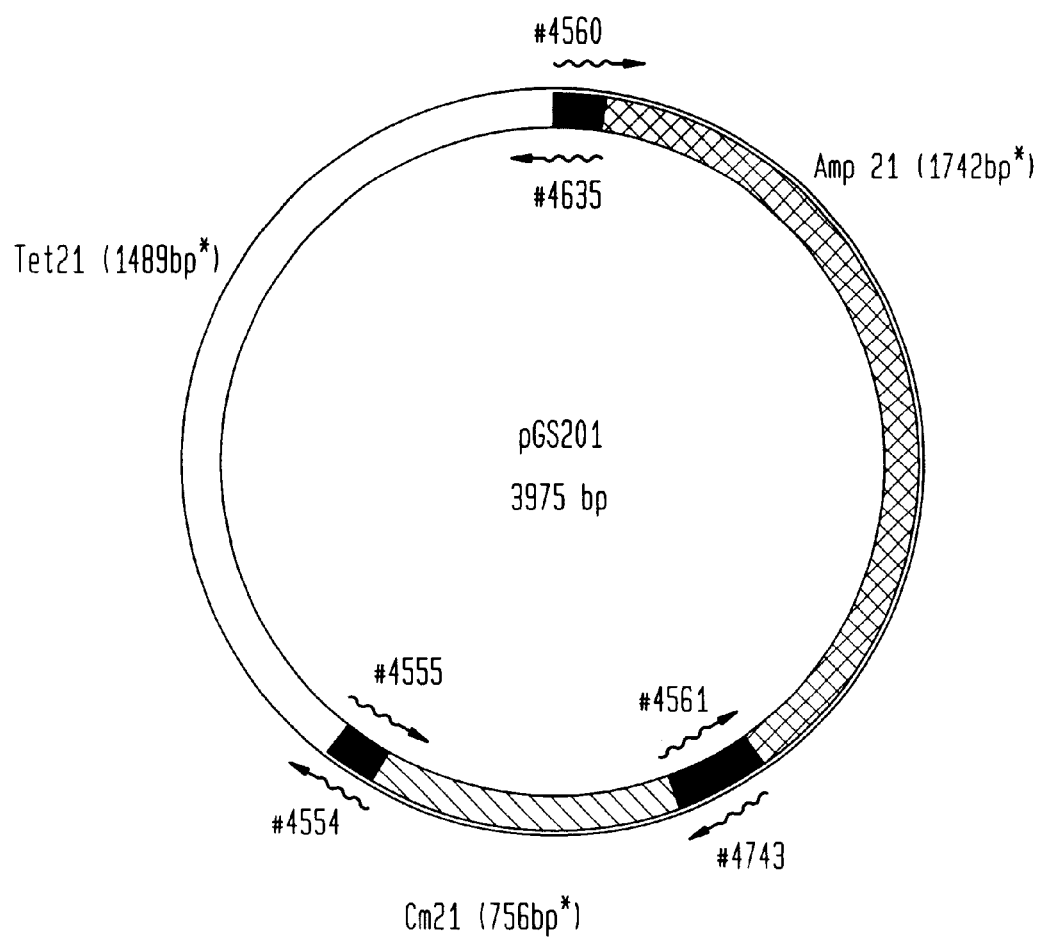
Figure 5:
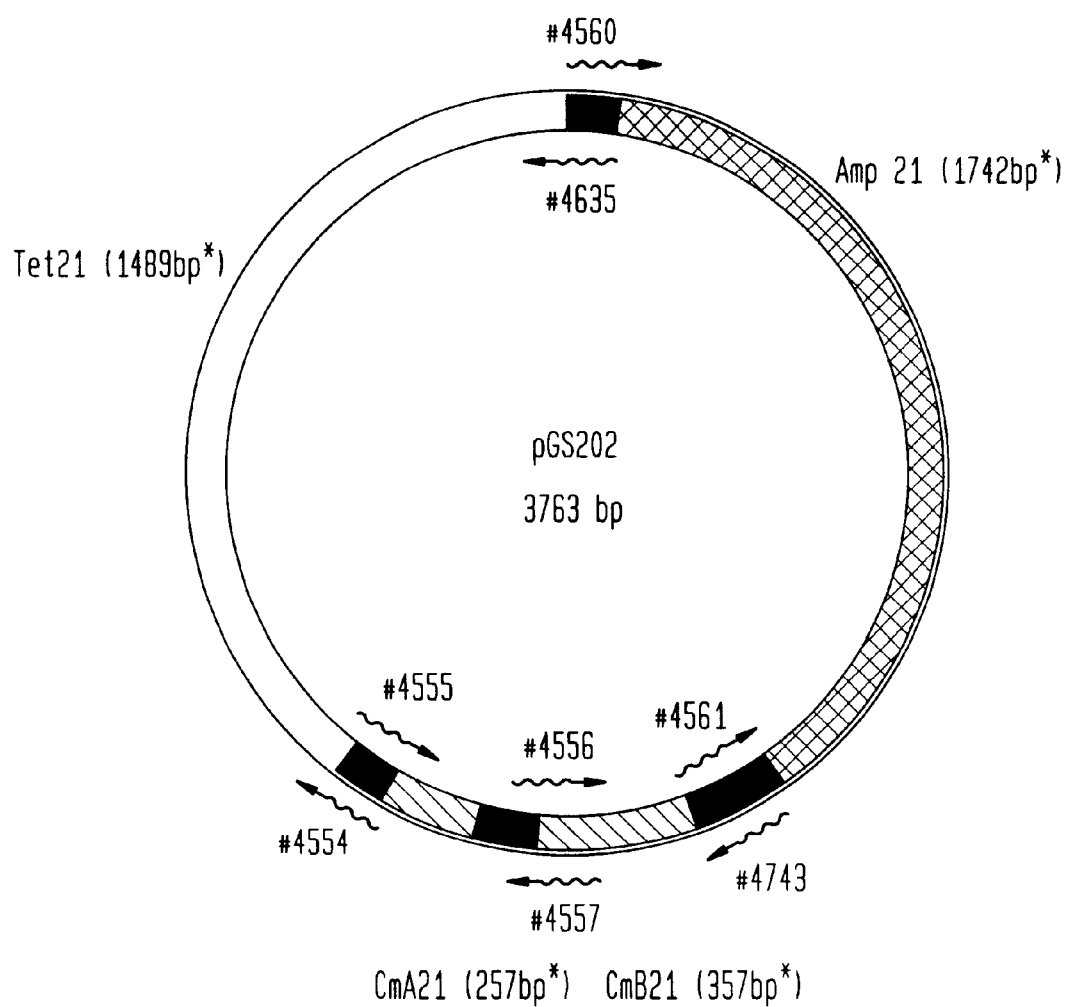
Figure 6:
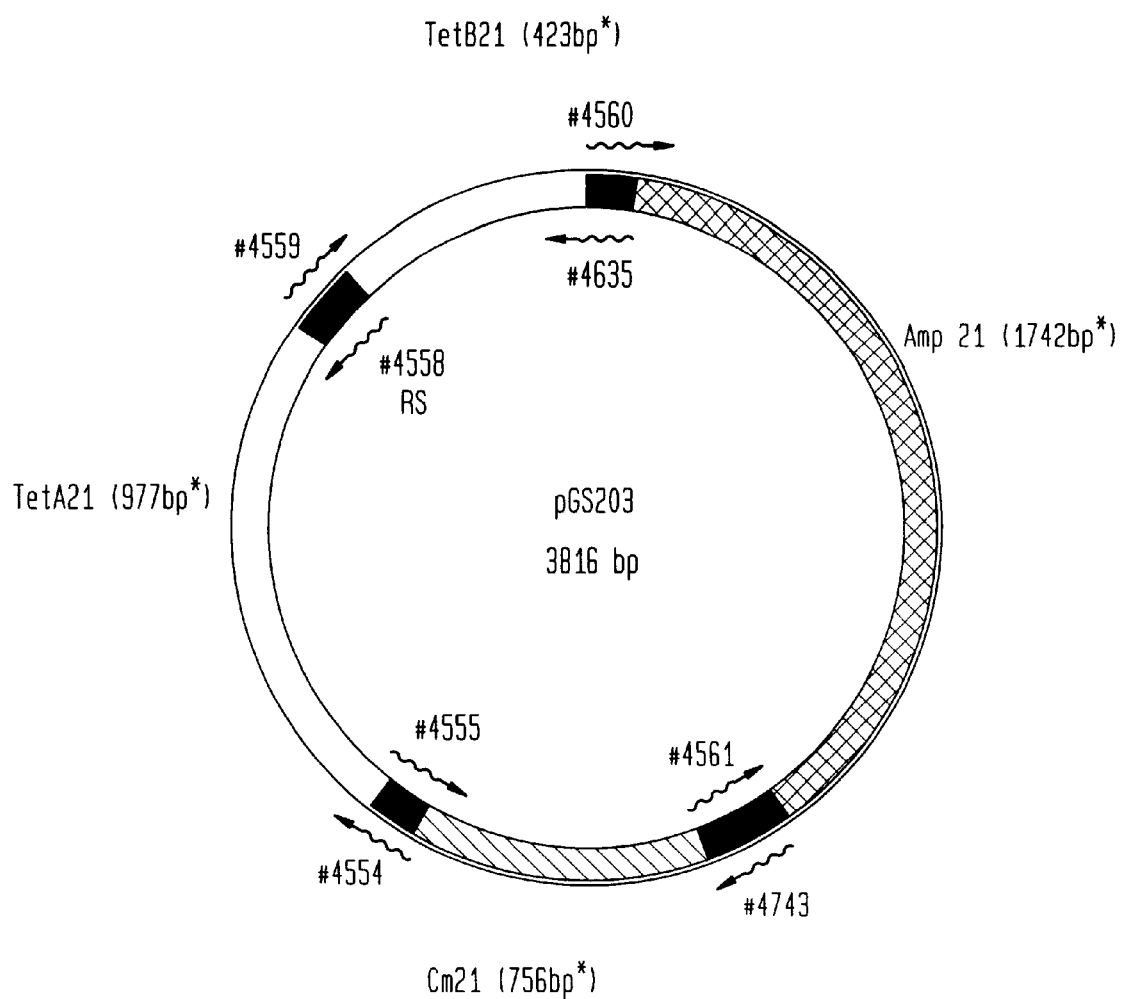

Two sets of plasmids were constructed, as depicted in FIGS. 1–6. In the first set, fragments containing 12 base overhangs were used (FIGS. 1–3). In the second, fragments containing 20–21 base overhangs were used (FIGS. 4–6).

Each set contained three plasmids:
1. A plasmid constructed out of the three basic fragments.
   an Amp$^r$ fragment (hereinafter Amp) which contained the Ampicillin resistance gene.
   a Tet$^r$ fragment (hereinafter Tet) which contained the Tetracycline resistance gene.
   a Cm$^r$ fragment (hereinafter Cm) which contained the Chloramphenicol resistance gene.
2. A plasmid constructed out of four fragments; the said Amp and Cm fragments and two fragments designated TetA and TetB, which are two separate regions of the Tet gene.
3. A plasmid constructed out of four fragments; the said Amp and Tet fragments and two fragments designated CmA and CmB, which are two separate regions of the Cm gene.

The plasmids of the first set are equivalent to the plasmids of the second set except for the length of the overhangs produced. The overhangs of the fragments were designed and produced by adding short repeats of either 3 or 5 bases. Each of the repeats in a set, was different and was complementary to one of the other repeats. The PCR fragments that were produced could therefore be connected to one another via the repeats to form a full circular plasmid (see FIGS. 1–6). Analogous primers of the two sets were nearly identical, the only difference being in the length of the repeat sequence. In the first set, the overall lengths of the repeats was 12 bp. In the second, the overall length of the repeats was 20–21 bp. In all cases, the dT residues in the repeats have been changed to dU residues. The 5' termini of fragments containing the repeats could therefore be dissociated from the complementary strand by a-purinating the dU residues, exposing a 3' overhang of the required size.

After amplifying the fragments comprising each plasmid they were mixed and their termini exposed utilizing UDG. After an annealing time period each mixture was used to transform bacterial cells, as detailed below.

A) Primers and PCR Conditions

Primers were synthesized with 3' ends that would enable generating PCR fragments from pBR322 and pACYC184 templates. The full sequence and maps of the various regions of these plasmids are well known and can be accessed from GenBank database under accession Nos. J01749 (pBR322), and X06403 (pACYC184). Two sets of primers were synthesized:

First Set of Primers: Primers Containing Repeats or Near-repeats of 12 Nucleotides with dUs at their 3' Ends Seq. ID NQ. 13 - Tet A sense
                                                     upstream of Tet (pBR322: 1–25)
-----12nt-----                       25nt
AU CAUAU CAUAU TTC TCA TGT TTG ACA GCT TAT CAT C
 *    *  *     *   *

Seq. ID NO. 15 - Tet A antisense
                                    downstream of Tet (pBR322: 913–937)
----12nt-----                        25nt
UA CUAUA CUAUA CAT GCC GGC GAT AAT GGC CTG CTT C
 *  *  *     *  *

Seq. ID NO. 16 - Tet B sense
                                          (pBR322: 1067–1091)
-----12nt-----                      25nt
UAUAG UAUAG UA GTA GAT GAC GAC CAT CAG GGA CAG C
 *  *    *  *     *

Seq. ID NO. 2 - Tet B antisense
///////downstream of Tet (pBR322: 1449–1425)
---12nt CUAx4--                    25nt
CUA CUA CUA CUA TGG CCA GGA CCC AAC GCT GCC CGA G
 *    *    *    *

Seq. ID NO. 18 - Amp sense
                               -upstream of.Amp (pBR322 2460-2483)
--12 bp AUGx4--                    24nt
AUG AUG AUG AUG AAC GCA GGA AAG AAC ATG TGA GCA
 *    *    *    *

Seq. ID NO. 8 - Amp antisense
                              -downstream of Amp (pBR322: 4159–4136)
--12 bp UAGx4--                      24nt
UAG UAG UAG UAG AAG AGT ATG AGT ATT CAA CAT TTC
 *    *    *    *

Seq. ID NO. 17 - Cm B sense
                                     -(pACYC184: 4086–4062)
----12bp------                     25nt
AU CUAAU CUAAU TAC GGT GAA AAC CTG GCC TAT TTC C
 *  *   *  *   *

Seq. ID NO. 14 - Cm B antisense
                                  downstream of Cm (pACYC184: 3768–3793)
---12nt CAUx4--                    26nt
CAU CAU CAU CAU CAG GCG TTT AAG GGC ACC AAT AAC TG
 *    *    *    *

Seq. ID NO. 25 - Cm A sense
(also designated 37102)
                             -upstream of Cm (pACYC184: 240–216
----12nt------                     25nt
AUAUG AUAUG AU TCA GGA GCT AAG GAA GCT AAA ATG G
 *   *  *    *

Seq. ID NO. 26 - Cm A antisense
(also designated 37105) -(pACYC184: 22–46)
----12bnt                                25nt
AAUUAG AUUAG AU CAG GCG GGC AAG AAT GTG AAT AAA G
            *

PCR REACTIONS

| reaction | Tet A12 | Tet B12 | Cm B12 | Cm A12 |
|---|---|---|---|---|
| 20 µl primer 1 | SEQ. ID 13 | SEQ. ID 16 | SEQ. ID 14 | SEQ. ID 25 |
| 20 µl primer 2 | SEQ. ID 15 | SEQ. ID 2 | SEQ. ID 17 | SEQ. ID 26 |
| (primer concentration: 0.1 µg/µl) | | | | |
| expected fragment size: | 961 bp | 406 bp | 340 bp | 241 bp |
| reaction | Tet 12 | Cm 12 | Amp 12 | |
| 20 µl primer 1 | SEQ. ID 13 | SEQ. ID 14 | SEQ. ID 18 | |
| 20 µl primer 2 | SEQ. ID 2 | SEQ. ID 25 | SEQ. ID 8 | |
| (primer concentration: 0.1 µg/µl) | | | | |
| expected fragment size | 1473 bp | 739 bp | 1724 bp | |
| mix | | x 128 | | |
| 2 µl dNTP's (2.5 mM each) | | 256 µl | | |
| 2.5 µl 10 × Buff. | | 320 µl | | |
| 18 µl H2O | | 2304 µl | | |
| 0.1 µl Taq (5 U/µl) | | 12.8 µl | | |
| put 360 µl mix in each tube. add primers | | | | |
| add 1 µl DNA (40 ng/µl): | Tet A12 | Tet B12 | Cm B12 | Cm A12 |
| | pBR322 | pBR322 | pACYC184 | pACYC84 |
| | Tet 12 | Cm 12 | Amp 12 | |
| | pBR322 | pACYC184 | pBR322 | |

Temperature regime
94° C. 40 sec
40° C. 2 min
72° C. 4 min
30 cycles
72° C. 5 min
6° C. infinitely Second Set of Primers: Primers Containing Repeats of 21 Nucleotides with dUs at their 3' Ends

```
SEQ. ID NO. 19 - TetA sense
                              -upstream of Tet (pBR322: 1-25)
------20nt CAUAUx4-----              25nt
CAUAU CAUAU CAUAU CAUAU TTC TCA TGT TTG ACA GCT TAT CAT C
  *  *   *  *   *  *   *  *

SEQ. ID NO. 5 TetB antisense
                            - downstream of Tet (pBR322: 1449-1425)
------21nt CUAx7----------           25nt
CUA CUA CUA CUA CUA CUA CUA TGG CCA GGA CCC AAC GCT GCC CGA G
 *   *   *   *   *   *   *

SEQ. ID NO. 21 - TetA antisense
                                       (pBR322: 913-937)
-----20nt CUAUAx4------              25nt
CUAUA CUAUA CUAUA CUAUA CAT GCC GGC GAT AAT GGC CTG CTT C
  * *   * *      *   * *

SEQ. ID NO. 22 - TetB sense
                                      -(pBR322: 1067-1091)
-----20nt UAUAGx4-----               25nt
UAUAG UAUAG UAUAG UAUAG GTA GAT GAC GAC GAT CAG GGA CAG C
 * *   * *   * *   * *

SEQ. ID NO. 20 - CmB antisense
                                      (pACYC184: 3768-3793)
------21nt CAUx7----------           26nt
CAU CAU CAU CAU CAU CAU CAU CAG GCG TTT AAG GGC ACC AAT AAC TG
 *   *   *   *   *   *   *

SEQ. ID NO. 27- CmA sense
(also designated 4555)      -(pACYC184: 240-216)
-----20nt AUAUGx4-----               25nt
AUAUG AUAUG AUAUG AUAUG TCA GGA GCT AAG GAA GCT AAA ATG G
 * *   * *   * *   * *

SEQ. ID NO. 28 - Cm A antisense
(also designated 4557)      -(pACYC184: 22-46)
-----20nt AUUAGx4-----               25nt
AUUAG AUUAG AUUAG AUUAG CAG GCG GGC AAG AAT GTG AAT AAA G
             
```

-continued

```
SEQ. ID NO. 23 - Cm B sense
                                      (pACYC 184: 4086-4062)
------20nt CUAAUx4------------------------25nt
CUAAU CUAAU CUAAU CUAAU TAC GGT GAA AAC CTG QCC TAT TTC C
  *     *     *     *    *   *   *   *   *   *   *   *

SEQ. ID NO. 11 - Amp antisense
                                      pBR322 (4159-4136)
------21nt UAGx7----------           24nt
UAG UAG UAG UAG UAG UAG UAG AAG AGT ATG AGT ATT CAA CAT TTC
 *   *   *   *   *   *   *

SEQ. ID NO. - 24 Amp sense
                                      pBR322 (2460-2483)
------21nt AUGx7-----------          24nt
AUG AUG AUG AUG AUG AUG AUG AAC GCA GGA AAG AAC ATG TGA GCA
 *   *   *   *   *   *   *
```

PCR REACTIONS

| reaction | Tet A21 | Tet B21 | Cm B21 | Cm A21 |
|---|---|---|---|---|
| 20 µl primer 1 | SEQ. ID 19 | SEQ. ID 22 | SEQ. ID 20 | SEQ. ID 28 |
| 20 µl primer 2 | SEQ. ID 21 | SEQ. ID 5 | SEQ. ID 23 | SEQ. ID 27 |
| (primer concentration: 0.1 µg/µl) | | | | |
| expected fragment size: | 977 bp | 423 bp | 357 bp | 257 bp |
| reaction | Tet 21 | Cm 21 | Amp 21 | |
| 20 µl primer 1 | SEQ. ID 19 | SEQ. ID 20 | SEQ. ID 11 | |
| 20 µl priemr 2 | SEQ. ID 5 | SEQ. ID 27 | SEQ. ID 24 | |
| (primer concentration: 0.1 µg/µl) | | | | |
| expected fragment size: | 1489 bp | 756 bp | 1742 bp | |
| mix | x 128 | | | |
| 2 µl dNTP's (2.5 mM each) | 256 µl | | | |
| 2.5 µl 10 × Buff. | 320 µl | | | |
| 18 µl H2O | 2304 µl | | | |
| 0.1 µl Taq (5 u/µl) | 12.8 µl | | | |
| put 360 µl mix in each tube. add primers | | | | |
| add 1 µl DNA (40 ng/µl) | Tet A21 | Tet B21 | Cm B21 | Cm A21 |
| | pBR322 | pBR322 | pACYC184 | pACYC84 |
| | Tet 21 | Cm 21 | Amp 21 | |
| | pBR322 | pACYC184 | pBR322 | |

Temperature regime

94° C. 40 sec

40° C. 2 min

72° C. 4 min 30 cycles

72° C. 5 min

6° C. infinitely

The required plasmids are illustrated in FIGS. 1 through 6. FIGS. 1–3 depict plasmids constructed from fragments containing 12 nucleotide (nt) overhangs. FIGS. 4–6 depicts plasmids constructed from fragments containing 21 nt overhangs.

B. Connecting the Fragments

The PCR fragments were mixed and their 3' overhangs exposed by utilizing UDG. The various reactions are given below. Two identical independent experiments were conducted. The DNA fragments for each experiment were prepared independently as well.

The concentration of the DNA fragments was 0.05 pmol/µl. UDG Buff.x10=200 mM Tris HCl pH 8.4, 500 mM KCl, 15 mM MgCl$_2$.

Reactions mixtures:

| | | | | | | | |
|---|---|---|---|---|---|---|---|
| 1. | 1 µl | 1 µl | 1 µl | 1 µl | 7 µl | 1.2 µl | 0.8 µl |
| | Amp 12 | Tet 12 | Cm 12 | H$_2$O | H$_2$O | UDG Buff. × 10 | UDG |
| 2. | 1 µl | 1 µl | 1 µl | 1 µl | 7 µl | 1.2 µl | 0.8 µl |
| | Amp 12 | Tet 12 | Cm A12 | Cm B12 | H$_2$O | UDG Buff. × 10 | UDG |
| 3. | 1 µl | 1 µl | 1 µl | 1 µl | 7 µl | 1.2 µl | 0.8 µl |
| | Amp 12 | Tet A12 | Tet B12 | Cm 12 | H$_2$O | UDG Buff. × 10 | UDG |
| 4. | 1 µl | 1 µl | 1 µl | 1 µl | 7 µl | 1.2 µl | 0.8 µl |
| | Amp 21 | Tet 21 | Cm 21 | H$_2$O | H$_2$O | UDG Buff. × 10 | UDG |

-continued

| 5. | 1 μl<br>Amp 21 | 1 μl<br>Tet 21 | 1 μl<br>Cm A21 | 1 μl<br>Cm B21 | 7 μl<br>H₂O | 1.2 μl<br>UDG Buff. × 10 | 0.8 μl<br>UDG |
|---|---|---|---|---|---|---|---|
| 6. | 1 μl<br>Amp 21 | 1 μl<br>Tet A21 | 1 μl<br>Tet B21 | 1 μl<br>Cm 21 | 7 μl<br>H₂O | 1.2 μl<br>UDG Buff. × 10 | 0.8 μl<br>UDG |

Figure 8A:
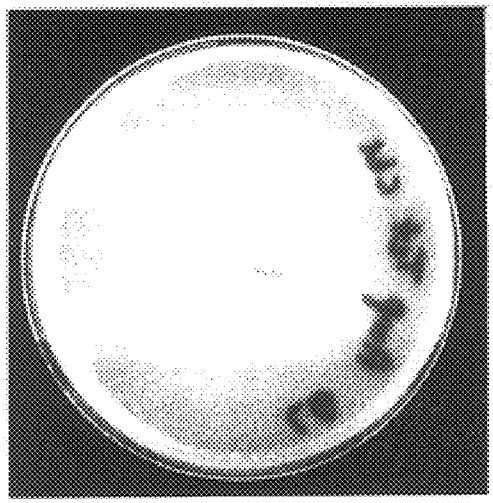
FIG. 8 shows the colonies that grew on plates following transformation with constructs illustrated in FIGS. 1–6. The results of constructs made with overhangs of 12 bases are shown on the left and those with overhangs of 20–21 bases are shown on the right.
Figure 8B:
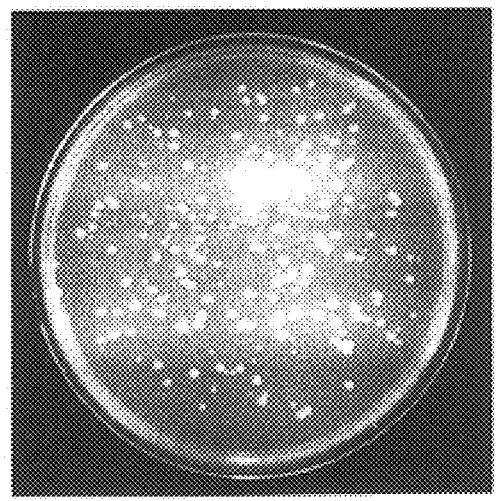
Figure 8C:
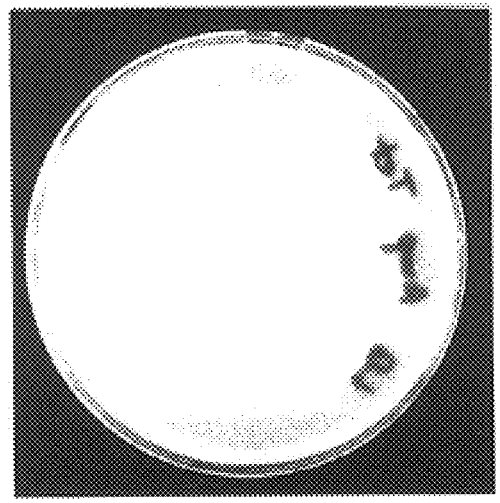
Figure 8D:
Figure 8E:
Figure 8F:
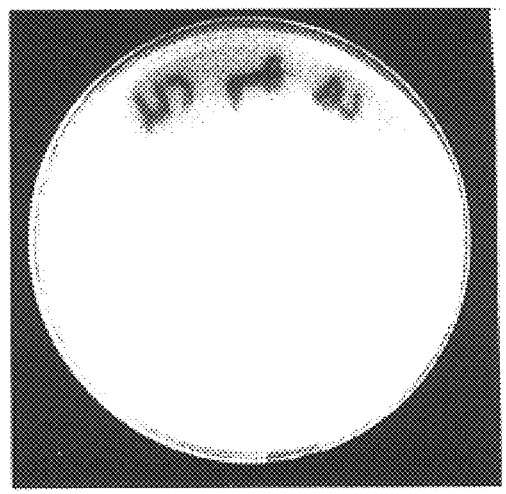

The reactions were incubated at 37° C. for 5 hours. 1 μl of each reaction was used in the electroporation of 20 μl GibcoBRL ElectroMax DH10B cells. After the transformation the cells of reactions 1 and 4 were plated on LB plates containing Ampicillin, Tetracycline and Chloramphenicol, for selection (FIGS. 8A and 8B respectively). Likewise, the cells of reactions 2 and 5 were plated on LB plates containing Ampicillin and Tetracycline (FIGS. 8C and 8D respectively). Cells of reactions 3 and 6 were plated on LB plates containing Ampicillin and Chloramphenicol (FIGS. 8E and 8F respectively). The fusion fragments CmA-CmB and TetA-TetB contain only the upstream and downstream fragments of $Cm^r$ and $Tet^r$. In addition they are interconnected by short linker repeats. They cannot therefore confer resistance to chloramphenicol or tetracycline.

846 An illustration of the constructs along with the number of transformants obtained, is given in FIG. 9. In the figure, colonies marked with a * were checked by PCR as detailed below and proven to contain plasmids with rearrangements rather than the required constructs.

Further Examination of the Constructs by PCR

The 6 transformants of reactions 2 as well as 16 representatives from reaction 5 were PCR tested in order to check whether they contain the desired constructs: Since these transformants were resistant to both Ampicillin and Tetracycline it was assumed that these fragments had fused correctly to each other. It was desired to know whether the Cm A and Cm B were present as well. Therefore the existence of the Cm fragments was tested by checking the various transformants by PCR with primers SEQ. ID NO. 14 and SEQ. ID NO. 25. Since in this constructs, Cm A (which encompasses part of the 5' region of Cm) is 257 bp long and Cm B (which encompasses part of the 3' region of Cm) is 357 bp long, the overall size of the expected PCR product should be 593 bp long, some 142 bp shorter than the size of a complete Cm fragment (756 bp long).

Figure 10A:
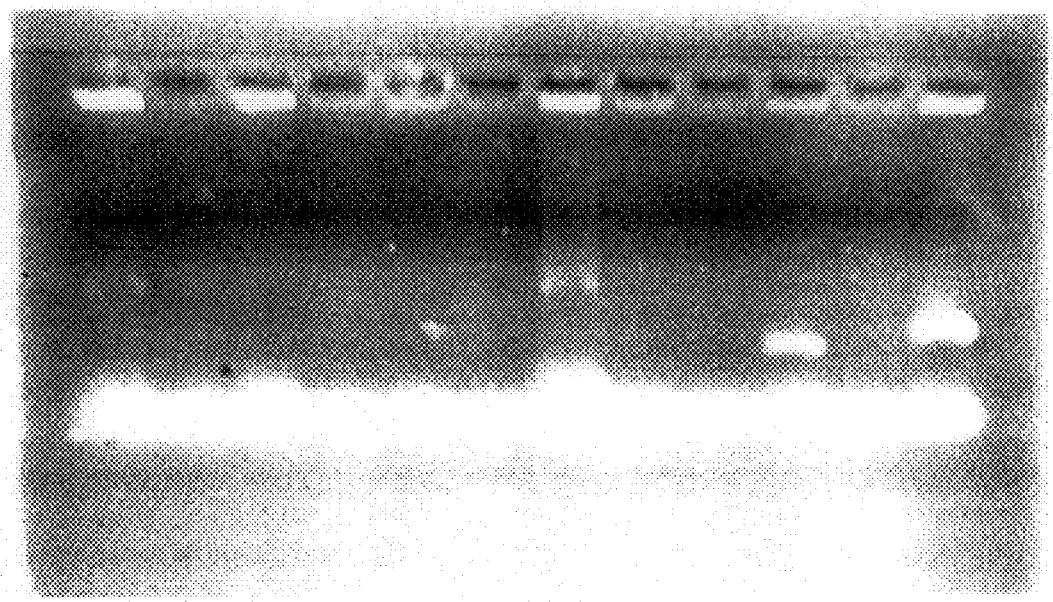
FIG. 10 shows the results of two gel runs of the products obtained in Example 3.

In FIG. 10(a), the six left lanes are of the transformants obtained from reaction 2, the next five lanes are from reaction 5. The right lane is a full Cm-fragment control.

Figure 10B:

In FIG. 10(b), the right lane is a full Cm-fragment control. The rest of the lanes are of more transformants from reaction 5.

The results indicate that none of the transformants in reaction 2 contain the desired constructs. In reaction 5, 9 out of 16 transformants contain the desired product.

Transformants from reactions 4, 5 and 6 were further tested by PCR to check if they contain the desired fragments in the desired order, as detailed below:

| reaction: | A<br>Tet | B<br>Cm A Tet A | C<br>Cm B Amp | D<br>Amp Tet B |
|---|---|---|---|---|
| primer 1 | SEQ. ID 13 | SEQ. ID 26 | SEQ. ID 17 | SEQ. ID 16 |
| primer 2 | SEQ. ID 2 | SEQ. ID 15 | SEQ. ID 8 | SEQ. ID 18 |
| expected fragment size: | 1473 bp | 1180 bp | 2043 bp | 1207 bp |

The tests carried out according to the above, verified that the transformants from reactions 5 and 6 (which were plasmids constructed from fragments having 21 nt overhangs) contained the desired fragments in the correct order. In reaction 5, 9 out of 16 transformants contained the desired product. In reaction 6, 2 out of 2 transformants contained the desired product.

This experiment clearly demonstrates the advantage of constructing plasmids from fragments with long overhangs (around 21 nt). Almost no colonies were obtained in the 3 experiments (1–3) that used fragments with overhangs of 12 nt. The only 6 colonies that were observed did not contain the correct construct. In contrast, in the experiments that used fragments with overhangs of 21 nt, colonies containing the correct product were readily obtained.

EXAMPLE 4

Assembly of Three DNA Fragments Using ExoII-created Overhangs

Exonuclease III (ExoIII) of *E. coli* was used in order to create complementary overhangs of 20 bases or longer. ExoIII digests one strand of blunt-ended DNA or DNA containing 5' overhangs, in a 3' to 5' direction, thus creating a 5' overhang or enlarging an existing 5' overhang. By regulating the temperature and time of the reaction one can control the extent of the digestion, hence the length of the overhang.

The formation of a construct made of three fragments is illustrated. Using the same method, plasmids made out of four and five segments were also constructed (not shown).

Figure 12:
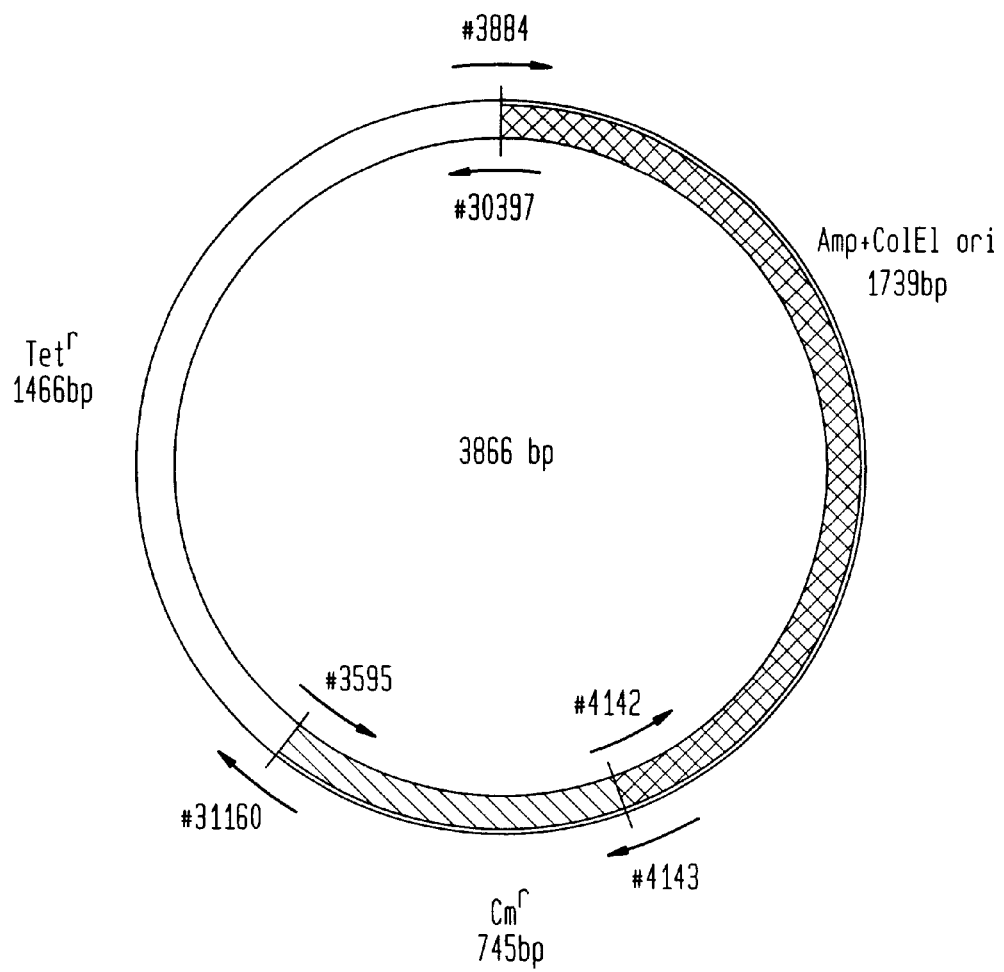
FIG. 12 illustrates the plasmid produced in example 4. The empty, cross-hatched and hatched bars have the above meanings. The arrows mark the primers which are used for the seamless junction of the fragments.

The plasmid illustrated in FIG. 12 was assembled by the joining of three independently produced DNA fragments. These three DNA fragments are:

a) a DNA fragment of 1739 base pairs (bp) containing the $Amp^r$ gene and the ColE1-ori region;

b) a DNA fragment of 1466 bp containing the $Tet^r$ gene; and c) a DNA fragment of 745 bp containing the $Cm^r$ gene.

These fragments are illustrated schematically in FIG. 12 showing their relative positioning one to the other, namely, that the $Cm^r$ fragment was to be connected at its one end to one end of the $Tet^r$ fragment and at its other end to one end of the $Amp^r$+Col1-ori fragment, and likewise, the other ends of the $Tet^r$ and $Amp^r$+CoE1-ori fragments were to be connected to each other to provide for a circular DNA molecule, being the desired plasmid, having the above predetermined order of the three fragments.

To produce the above three DNA fragments, the aforementioned PCR procedure was carried out using the following primers and template DNA:

a) The 1739 bp $Amp^r$+ColE1-ori DNA fragment was synthesized by the PCR procedure using primers SEQ. ID NO. 29 (also designated 4142) and SEQ. ID NO 30 (also designated 3884) and pBR322 as the template DNA. The concentrations of the primers and template DNA, as well as the other PCR conditions, are as indicated above. The relative direction of the primers with respect to the synthesis of the $Amp^r$+ColE1-ori fragment as it is positioned in the completed plasmid product is as depicted schematically in FIG. 12. Thus, primer SEQ. ID NO. 29 was synthesized to have a predetermined sequence so as to provide for the desired junction region between the $Amp^r$+ColE1-ori fragment and the $Cm^r$ fragment, and primer SEQ. ID NO. 30 was synthesized to have a predetermined sequence so as to provide for the desired junction between the Amp$^r$+ColE1-ORI fragment and the Tet$^r$ fragment.

b) The 1466 bp Tet$^r$ DNA fragment was synthesized by the PCR procedure using primers SEQ. ID NO. 31 (also designated 31160) and SEQ. ID NO. 32 (also designated 30397) and pBR322 as the template DNA. The concentrations of the primers and template DNA, as well as the other PCR conditions, are as indicated above. The relative direction of the primers with respect to the synthesis of the Tet$^r$ fragment as it is positioned in the completed plasmid product is as depicted schematically in FIG. 12.

c) The 745 bp Cm$^r$ DNA fragment was synthesized by the PCR procedure using primers SEQ. ID NO. 33 (also designated 3595) and SEQ. ID NO. 34 (also designated 4143) and pACYC184 as the template DNA. The relative direction of the primers with respect to the synthesis of the Cm$^r$ fragment as it is positioned in the completed plasmid product is as depicted schematically in FIG. 12.

The sequences of the above primers are as follows:
The arrows inside the sequences mark the junction points.

primers SEQ. ID NO. 29 and SEQ. ID NO. 30
for the Amp$^r$+ColE1-ori segment:

Once purified, each PCR fragment was then quantitated by determining the DNA concentration of each fragment by standard procedures, using Pharmacia's Gene-Quant™ RNA/DNA calculator and following the manufacturer's instructions.

The PCR fragments were then subjected to Exo III digestion and subsequent joining procedure. The various PCR fragments were mixed together (0.15 pmol DNA for each fragment), in a cooled (6° C.) reaction mixture of 12 μl containing: 1.2 μl 10×TA buffer (330 mM Tris-acetate, pH 7.8: 660 mM potassium acetate, 100 mM magnesium acetate and 5 mM DTT); 0.8 μl Exo III (200 U/μl purchased from Epicentre Technologies); and sterile double distilled H$_2$O to make up the final volume of 12 μl. In practice, the PCR fragments were mixed into a precooled, namely, 6° C., TA buffer solution made up to 11.2 lll with the H$_2$O, to which was then added the 0.8 μl Exo III. Adding the Exo III last provides for better control over the Exo III reaction, which is controlled by the time of incubation of the PCR fragments with the Exo III. Following the Exo III addition, the reaction mixture was then incubated at 6° C. for 40 mins (the time necessary to achieve more than 20 nucleotide degradation of each DNA strand in the 3'–5' direction under the above conditions of temperature=6° C. and concentration of Exo III).

```
primers SEQ. ID NO. 29 and SEQ. ID NO. 30
for the Amp^r +ColE1-ori segment:

part of Cm^r region sequence      part of Amp^r region sequence
primer SEQ. ID NO. 29: ATTGGTGCCCTTAAACGCCTG↓AACGCAGGAAAGAACATGTG
(also designated 4142)

part of Tet^r region sequence        part of Amp^r region sequence
primer SEQ. ID NO. 30: AGCGTTGGGTCCTGG↓CCAAAGAGTATGAGTATTCAACA
(also designated 3884)

primers SEQ. ID NO. 31 and SEQ. ID NO. 32
for the Tet^r segment:

part of
          Cm^r region sequence     part of Tet^r region sequence
primer SEQ. ID NO. 31: AGCTCCTGA↓TTCTCATGTTTGACAGCTTATC
(also designated 31160)

part of
          Amp^r + ColE1-ori
          region sequence      part of Tet^r region sequence
primer SEQ. ID NO. 32: ATACTCTT↓TGGCCAGGACCCAACGCTGCCC
(also designated 30397)

primers SEQ. ID NO. 33 and SEQ. ID NO. 34
for the Cm^r segment:

part of
                Tetr region
                sequence         part of Cm^r region sequence
primer SEQ. ID NO. 33: AAACATGAGAA↓TCAGGAGCTAAGGAAGCTAAAATG
(also designated 3595)

The Amp region    The CM region
primer SEQ. ID NO. 34: ATGTTCTTTCCTGCGTT↓CAGGCGTTTAAGGGCACCAATAAC
(also designated 4143)
```

In view of the fact that the original primer sequences were derived only from the Tet$^r$, Cm$^r$ and Amp$^r$+ColE1-ori region genes, with no introduction of any additional ("linker") DNA sequences whatsoever, the above junctions between said genes are "seamless".

The PCR was carried out according to the description in the former examples. Each PCR fragment, separately, was then subjected to agarose-gel purification using a commercial kit, namely, Bio-Rad's Prep-A-Gene™ purification kit and following the manufacturer's instructions.

The Exo III reaction was then stopped by performing a phenol extraction. This is done by adding to the above reaction mixture an equal volume=12 μl of a 1:1 (v/v) phenol/chloroform mixture which causes denaturation of the Exo III. The aqueous phase was then separated from the above phenol/chloroform mixture, this aqueous phase contains the PCR fragments. The separated aqueous phase was then subjected to three washes with chloroform to yield a final aqueous phase having an essentially purified mixture of the Exo III-digested PCR fragments.

In order to prevent both the evaporation of the buffer and the drying of the fragments. 40 µl of mineral oil was added to the vessel containing the Exo III-digested PCR fragments. The mixture was then heated to 75° C., at which temperature it was further incubated for one hour. After this incubation, the mixture is slowly cooled, under conditions providing only a 2° C. decrease in temperature per hour, until it reached 37° C. (the heating and cooling to provide for specific complementary interactions between complementary overhangs on the PCR fragments and to prevent non-specific interactions). This heating and cooling represents the first stage of the specific joining between the fragments, the joining by way of hydrogen bonding between complementary overhangs.

Once the above mixture has reached 37° C., it was then subjected to the final stage of the joining, including the filling in reaction, as follows:

To the cooled (at 37° C.) mixture of now essentially joined (by hydrogen bonding of complementary overhangs) PCR fragments there was added 10 µl of the 'Synthesis Mixture', which contains:

1 µl of 20 mM ATP

4 µl of 2.5 mM dNTPs (=dATP, dTTP, dCTP and dGTP in equal amounts, concentration of each 32 2.5 mM)

1 µl of 10×TA buffer (see above for constituents)

1 µl of T7 DNA polymerase (5 U/µl, purchased from USB)

1 µl of T4 DNA ligase (10 U/µl, purchased from Epicentre Technologies)

2 µl of sterile double-distilled $H_2O$

Total volume: 10 µl

The above synthesis mixture had the T7 DNA polymerase and dNTPs to facilitate the filling in of gaps in the junction regions between the joined fragments, as well as the ATP and the T4 ligase to covalently join the DNA strands together once the filing in of gaps has been completed.

Following the addition of the synthesis mixture, the resulting reaction mixture was then incubated for two hours at 37° C. After this incubation, the reaction mixture was then ethanol precipitated under standard conditions to finally yield a pellet of precipitated DNA which was essentially the completed DNA construct composed of the joined PCR fragments. This DNA pellet was resuspended in 5 µl sterile double-distilled $H_2O$ and is ready for further analysis or use.

Following the preparation of the desired construct described above from the three PCR fragments, this construct was analyzed for its biological activity, namely, whether or not it could confer resistance to all three antibiotics when introduced into bacterial cells. Thus, electroporation of electrocompetent DH10B $E.$ $coli$ cells was performed using a 2 µl aliquot of a 5 µl final product containing the DNA construct. After electroporation, the cells were first plated on agar plates containing ampicillin. The results revealed more than 1000 colonies on these plates, indicating that more than 1000 originally transformed cells received a DNA construct having at least an active $Amp^r$ gene. Of these $Amp^r$ colonies, 40 were chosen at random, as a test sample, and were plated on both tetracycline- and chloramphenicol-containing agar plates. All 40 of these test colonies grew on these plates as well, indicating that they were also $Tet^r$ and $Cm^r$.

Hence, it is concluded that at least these 40 colonies received an intact construct in which all of the $Tet^r$, $Cm^r$ and $Amp^r$ genes were intact and fully expressible. Some of the colonies were tested further by PCR, as indicated above. The PCR bands that appeared were of the expected sizes.

In the above example, the ligation and fill-in steps have been used for the sake of completeness and to illustrate possible alternative procedures. However, as will be easily understood by the skilled person, said ligation and fill-in steps are not necessary, and the procedure exemplified above can be carried out without using such steps. Examples of such procedures without said steps have not been given, for the sake of brevity.

EXAMPLE 5

Assembly of 8 DNA Fragments into a Circularized Plasmid Using UDG-created Overhangs The plasmid to be constructed was designed to consist of eight fragments, each to be prepared separately by PCR amplification and then joined in a specific directional fashion to provide a circularized plasmid as the end-product. For the purposes of exemplifying the method of the present invention, it was chosen to combine eight PCR fragments which together encompass four regions, as detailed below, thus carrying out a specific directional connection of eight independent PCR fragments to form a single active plasmid construct, and this by an essentially one-step procedure in accordance with the present invention, a result never obtained or attempted in the prior art.

This example is similar to Example 1, as the overhangs are created by the use of dU in the primer and the enzyme UDG to expose the overhang. However, in the present example, only one dU residue per primer is used. Therefore, the procedure of exposing the overhang comprises an additional reagent. N,N Dimethyl-ethylenediamine. The use of this reagent is explained in further detail in the section of general procedures above and in the above mentioned copending patent application, identified as Attorney Docket 4149/96, Israeli Patent Application No. 120337. In addition, the present example uses primers that contain, at their 5' end, the natural gene sequence of the fragment to which they are to be joined. The junction is therefore seamless: no unnecessary residues are added at the junctions. In contrast, Example 1 uses primers that contain at their 5' end an irrelevant sequence whose only purpose is to serve as an overhang, since several dU residues must be used in the 5' part of the primer sequence. This irrelevant sequence is then introduced into the resulting fragment between the natural gene sequences of the fragments that are joined. Thus, the use of only one dU nucleotide, as in the present example, enables the seamless joining of fragments.

Figure 13:
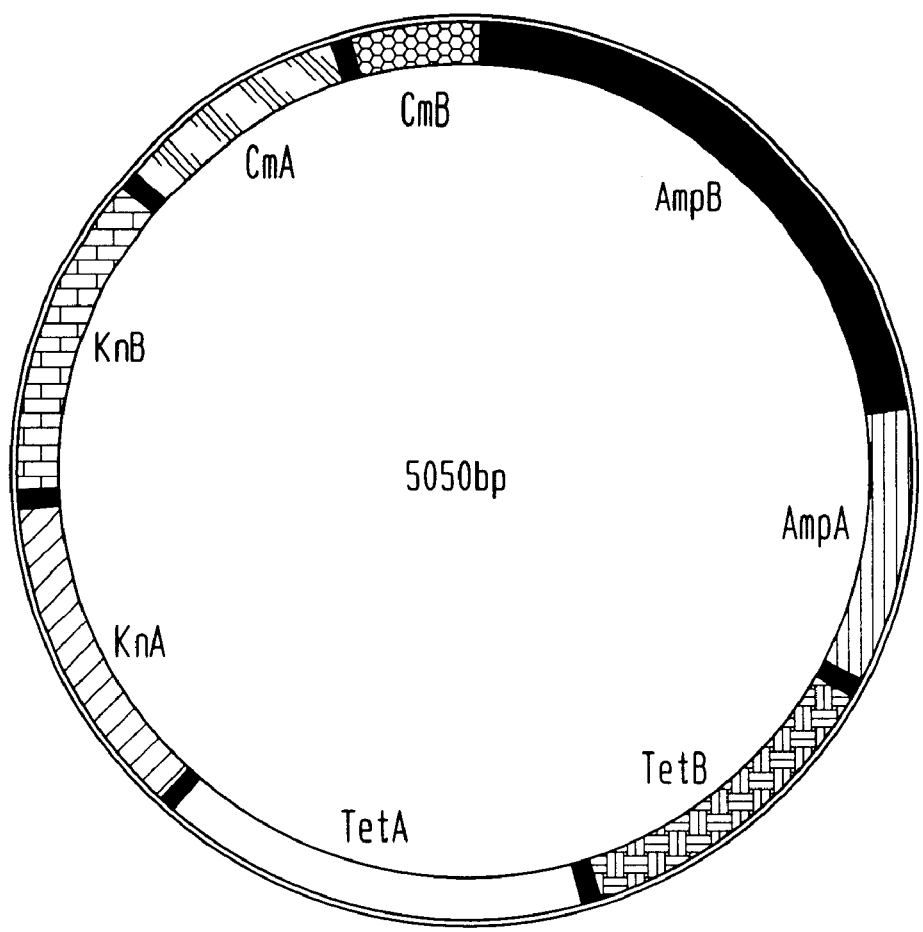
FIG. 13 shows a construct made by joining 8 different fragments in the experiment of example 5.

In FIG. 13, there is shown schematically the plasmid that was designed and produced by the method of the present invention. This plasmid carries four independent antibiotic resistance genes, for resistance to Ampicillin ($Amp^r$ gene, or hereinafter Amp); Tetracycline ($Tet^r$ gene, or hereinafter Tet); Chloramphenicol ($Cm^r$ gene, or hereinafter Cm) and Kanamycin ($Kn^r$ gene, or hereinafter Kn). The plasmid also carries the ColE1 origin of replication (ColE1-ori), which in this specific instance is situated next to the $Amp^r$ gene. Hence, such a plasmid is capable of being replicated in a host cell and will endow the host cell with resistance to all four types of antibiotic.

Accordingly, it is possible to readily select for those host cells transformed by this plasmid by growing the transform cells in the presence of one of the antibiotics and then to screen for the resistance to the other antibiotics. In order to verify that mis-connections did not occur, additional verification tests may be carried out. One such test carried out included testing transformed colonies by restriction enzyme analysis.

Plasmid DNA was prepared from a number of transformed colonies and checked by restriction enzymes.

For this eight fragments construction, the following was carried out:
(i) Preparation of the Specific Primers for the PCR Amplification.

As shown in FIG. 13, and as outlined above, it was desired to construct a circularized plasmid having four regions:
(a) a Tet$^r$ region.
(b) an Amp$^r$+ColE1-ori region.
(c) a Cm$^r$ region.
(d) a Kn$^r$ region.

The order of the connection is depicted in FIG. 13.

To achieve this task, eight separate fragments were designed:

| Name of fragment |  |  |  |  | Size (bp) | plasmid | Location |
|---|---|---|---|---|---|---|---|
| AmpA |  |  |  | 241365 | 574 | pBR322 | 3603–4159 |
| AmpB | 27342 |  |  | 3885 | 1171 | pBR322 | 2460–3624 |
| CmA | 40122 |  |  | 241366 | 481 | PACYC1 | 4021–240 |
| CmB |  | 27343 25596 |  |  | 293 | PACYC1 | 3768–4043 |
| TetA |  | 27341 | 4144 |  | 862 | pBR322 | 1–848 |
| TetB | 30402 |  |  | 36176 | 631 | pBR322 | 827–1449 |
| KnA | 31254 | 25595 |  |  | 569 | PACYC1 | 1809–2368 |
| KnB |  | 25953 25952 |  |  | 652 | PACYC1 | 2349–2991 |
|  |  |  |  | 31253 |  |  |  |

Written are the names of the fragments, their sizes, the plasmid from which they were PCR amplified, the exact location on the original plasmid of the site to be amplified and the numbers of the primers that were used to amplify the fragments. The full sequence and maps of the various regions of these plasmids are well known and can be accessed from GenBank database under accession Nos. J01749 (pBR322), X06403 (pACYC184) and X06402 (pACYC177).

The AmpB fragment includes the 5' part of the Amp fragment and the ColE1-ori sequence. The AmpA fragment includes the 3' part of the Amp fragment. The CmA fragment includes the 5' part of the Cm fragment and the CmB fragment includes the 3' part of the Cm fragment. The TetB fragment includes the 5' part of the Tet fragment and the TetA fragment includes the 3' part of the Tet fragment. The KnA fragment includes the 5[<b>old40 part of the Kn fragment and the KnB fragment includes the 3' part of the Kn fragment.

Each primer consists of two regions: a 3' region complementary to the DNA to be amplified, and a 5' region complementary to the fragment it should be connected to.

Using standard automated procedures to produce polynucleotide oligomers (Applied Biosystems, U.S.A.), the following primers were synthesized:

Primers for the Amplification of the AmpA Fragments
primer SEQ. ID NO. 35, also designated 241365:
internal Amp$^r$ region

```
Primers for the amplification of the AmpA
fragments primer SEQ. ID NO. 35, also designated 241365:
ATTGCTGCAGGCATCGTGGTGUCA
                        * primer SEQ. ID NO. 36, also designated. 3885:
   Cmr region        Ampr region
AGCGTTGGGTCCTGGCCA-AAGAGTAUGAGTATTCAA
                  *
```

-continued
```
Primers for the amplification of the AmpB
fragments primer SEQ. ID NO. 37, also designated 27342:
Cmr region       Ampr region
   ACGCCTG-AACGCAGGAAAGAACAUGTG
          * primer SEQ. ID NO. 38, also designated 241366:
   internal Ampr region
ACACCACGATGCCTGCAGCAAUGG
                       *

Primers for the amplification of the CmA fragments primer SEQ. ID NO. 39, also designated 40122:
      Knr region         Cmr region
AGG CCT GGT ATG AGT C - TCA GGA GCU AAG GAA GCT
                     *

AAA ATG primer SEQ. ID NO. 40, also designated 27343:
     internal Cmr region
ATTGGCTGAGACGAAAAACATAUTCTC
                          *
```

-continued

Primers for the amplification of the CmB fragment primer SEQ. ID NO. 41, also designated 25596:
    internal Cmr region
ATATGTTTTTCGTCTCAGCCAAUCC
                        * primer SEQ. ID NO. 42; also designated 4144:
    Ampr region          Cmr region
ATGTTCTTTCCTGCGTT-CAGGCGUTTAAGGGCACCAATAAC
                *

Primers for the amplification of the TetA
fragment:

primer SEQ. ID NO. 43, also designated 27341:
    internal Tetr region
ATACCGCAAGCGACAGGCCGAUCATCG
                          * primer SEQ. ID NO. 44, also designated 36176:
    Kn antisense         Tet sense
ACGTGGCTTTGTTG-TTCTCATGUTTGACAGCTTATC
             *

Primers for the amplification of the TetB
fragment:

primer SEQ. ID NO. 45, also designated 30402:
Ampr region           Tetr region
    ATACTCTT-TGGCCAGGACCCAACGCUGCCC
                                 * primer SEQ. ID NO. 46, also designated 25595:
    internal Tetr region
ATCGGCCTGTCGCTTGCGGTAUTCG
                        *

Primers for the amplification of the KnA fragment:

primer SEQ. ID NO. 47, also designated 31254:
Tet region        Kn region
 ACATGAGAA-CAACAAAGCCACGUTGTGTCTC
                                * primer SEQ. ID NO. 48, also designated 25953:
    internal Kn region
AGACGAAATACGCGATCGCUGTTAA
                        *

Primers for the amplification of the KnB fragment:

primer SEQ. ID NO. 49, also designated 25952:
    internal Kn region
AGCGATCGCGTATTTCGTCUCGCTC
                        * primer SEQ. ID NO. 50, also designated 31253:
Cm region       Kn region
AGCTCCTGA-GACTCATACCAGGCCUGAATCG
                              *

(ii) Preparation of the PCR Fragments

PCR reactions were carried out as in the other examples above. Following PCR synthesis of the individual fragments, each fragment was purified by standard agarose-gel purification techniques using the commercially available Bio-Rad "Prep-A-Gene™" DNA purification kit and adhering to the manufacturer's instructions. Following purification, the concentration of the purified fragment DNA was determined by standard procedures using the Pharmacia "Gene-Quant™ RNA/DNA Calculator" and adhering to the manufacturer's instructions.

(iii) Connection of the PCR-produced Fragments

The eight PCR fragments as produced and purified according to the above-mentioned procedure, were connected to each other in a one-step reaction mixture in a single reaction vessel. This was achieved by mixing the fragments together in a 25 µl reaction mixture that included: 0.15 pmol of each fragment, 2.5 µl buffer (200 mM Tris-HCl pH 8.4, 500 mM KCl, 15 mM $MgCl_2$), 2.5 µl of 1M N,N-Dimethyl-ethylenediamine and 6.25 units of UDG (GibcoBRL). The mixture was incubated at 37° C. for 4 hours and then transferred to 70° C. for 5 minutes to facilitate dissociation of the short nicked single-stranded DNA from the 5' ends of the fragments. After dissociation the short nicked single-stranded DNA were removed using "QIAquick PCR purification kit" (QIAGEN) adhering to the manufacturer's instructions. Before adding the first buffer of the kit, 200 µl of hot (70° C.) buffer (20 mM Tris-HCl pH 8.4, 50 mM KCl, 1.5 mM $MgCl_2$) was added in order to minimize the reannealing of the short nicked single-stranded DNA. The DNA was eluted in 30 µl of double-distilled water (DDW). 27 µl of the DNA was incubated with 3 µl of buffer (20 mM Tris-HCl pH 8.4, 50 mM KCl, 1.5 mM $MgCl_2$) in a water-bath, at 70° C. The bath was shut down and the temperature was slowly decreased to 37° C. This allows for the joining between the complementary overhangs, while minimizing illegitimate connection.

(iv) Analysis of the Efficiency of Joining of the Fragments

A 1 µl sample of the above DNA, containing the newly constructed plasmid, made from joining the 8 separate fragments, was used to transform E. coli DH10B cells by electroporation. In the transformation procedure 20 µl of electrocompetent "ElectroMax" cells (purchased from Gibco BRL) were mixed with the above DNA sample and subjected to electroporation in a commercially available apparatus (BioRad "E. coli Pulser Apparatus" set at 1.8 kV and operated according to the manufacturer's instructions).

Following electroporation (transformation) the cells were plated on LB Agar plate containing 100 mM Ampicillin (to select for transformants having Ampicillin resistance by virtue of having being transformed with a DNA carrying the $Amp^r$ gene). On the day after, three colonies were picked and checked for resistance to Chloramphenicol, Tetracycline and Kanamycin by plating on Agar plates containing the appropriate antibiotics.

The results showed that the three colonies were resistant to all the four antibiotics. The colonies were further checked by restriction enzyme analysis and proved to be correct (data not shown).

The above result is very significant since it shows that it is possible to join correctly 8 separate DNA fragments in a specific directional manner, in a single reaction mixture by an essentially one-step procedure.

All the above description of preferred embodiments and examples have been provided for the purpose of illustration, and are not meant to limit the invention. Many modifications can be made in the methods, materials and conditions, and many different products and results can be obtained, using different numbers of overhangs and different numbers of fragments to be joined, all without exceeding the scope of the invention.

What is claimed is:

1. A method for assembling a plurality of DNA fragments comprising:
   a) providing at least one first double stranded DNA fragment having at least one terminal single stranded overhang having from 15 to about 30 bases;
   b) providing at least one second double stranded DNA fragment having at least one terminal single stranded overhang having from 15 to about 30 bases complementary to the overhang of a); and
   c) mixing said first and second DNA fragments in a molar ratio of from about 1:1 to about 1:50 under conditions suitable to promote specific joining thereof.

2. The method of claim 1, wherein at least three DNA fragments are joined.

3. A method for assembling a plurality of DNA fragments comprising:
   a) providing at least one first double stranded DNA fragment having at least one terminal single stranded overhang having about 15 to about 30 bases;
   b) providing at least one second double stranded DNA fragment having at least one terminal single stranded overhang having from 15 to about 30 bases complementary to the overhang of a);
   c) providing at least one third double stranded DNA fragment having at least one terminal single stranded overhang having from 15 to about 30 bases complementary to the overhang of b); and
   d) mixing said first, second and third DNA fragments under conditions suitable to promote specific joining thereof.

4. The method of claim 3, wherein more than three DNA fragments are joined.

5. A method for assembling a plurality of DNA fragments comprising:
   a) providing at least one first double stranded DNA fragment having at least one terminal single stranded overhang having from 15 to about 30 bases;
   b) providing at least one second double stranded DNA fragment having at least one terminal single stranded overhang from 15 to about 30 bases complementary to the overhang of a);
   c) providing at least one third double stranded DNA fragment having at least one terminal single stranded overhang having from 15 to about 30 bases complementary to an overhang of b); and
   d) mixing said first, second and third DNA fragments in a molar ratio of from about 1:1 to about 1:50 under conditions suitable to promote specific joining thereof.

6. A method of assembling a plurality of DNA fragments comprising:
   a) providing at least one first double stranded DNA fragment having at least one terminal single stranded overhang having from 20 bases to about 30 bases;
   b) providing at least one second double stranded DNA fragment having at least one terminal single stranded overhang having from 20 to about 30 bases complementary to the overhang of a); and
   c) mixing said first and second DNA fragments in a molar ratio of from about 1:1 to about 1:50 under conditions suitable to promote specific joining thereof.

7. The method of claim 6, wherein more than three DNA fragments are joined.

8. A method for assembling a plurality of DNA fragments comprising:
   a) providing at least one first double stranded DNA fragment having at least one terminal single stranded overhang having from 20 to about 30 bases;
   b) providing at least one second double stranded DNA fragment having at least one terminal single stranded overhang having from 20 to about 30 bases complementary to the overhang of a);
   c) providing at least one third double stranded DNA fragment having at least one terminal single stranded overhang having from 20 to about 30 bases complementary to an overhang of b); and
   d) mixing said first, second and third DNA fragments under conditions suitable to promote specific joining thereof.

9. The method of claim 8, wherein more than three DNA fragments are joined.

10. The method of claim 8, wherein more than three DNA fragments are joined.

11. A method for assembling a plurality of DNA fragments comprising:
   a) providing at least one first double stranded DNA fragment having at least one terminal single stranded overhang having from 20 to about 30 bases;
   b) providing at least one second double stranded DNA fragment having at least one terminal single stranded overhang having from 20 to about 30 bases complementary to the overhang of a);
   c) providing at least one third double stranded DNA fragment having at least one terminal single stranded overhang having from 20 to about 30 bases complementary to an overhang of b); and
   d) mixing said first, second and third DNA fragments in a molar ratio of from about 1:1 to about 1:50 under conditions suitable to promote specific joining thereof.

12. The method of claim 11, wherein more than three DNA fragments are joined.

13. A method for assembling a plurality of DNA fragments comprising:
   a) providing at least one first double stranded DNA fragment having at least one terminal single stranded overhang having from about 20 to about 30 bases;
   b) providing at least one second double stranded DNA fragment having at least one terminal single stranded overhang having from about 20 to about 30 bases complementary to the overhang of a); and
   c) mixing said first and second DNA fragments in a molar ratio of from about 1:1 to about 1:50 under conditions suitable to promote specific joining thereof.

14. The method of claim 13 wherein at least three DNA fragments are joined.

15. The method of claim 13 wherein the single stranded overhangs of the first and second double stranded DNA fragments having from 21 to 30 bases.

16. A method for assembling a plurality of DNA fragments comprising:
   a) providing at least one first double stranded DNA fragment having at least one terminal single stranded overhang having from about 20 to about 30 bases;
   b) providing at least one second double stranded DNA fragment having at least one terminal single stranded overhang having from about 20 to about 30 bases complementary to the overhang of a);
   c) providing at least one third double stranded DNA fragment having at least one terminal single stranded overhang having from about 20 to about 30 bases complementary to an overhang b); and
   d) mixing said first, second and third DNA fragments under conditions suitable to promote specific joining thereof.

17. The method of claim 16 wherein more than three DNA fragments are joined.

18. The method of claim 16 wherein the single stranded overhangs of the first, second and third double stranded DNA fragments each have from 21 to 30 bases.

19. A method of assembling a plurality of DNA fragments comprising:
   a) providing at least one first double stranded DNA fragment having at least one terminal single stranded overhang having from about 20 to about 30 bases;
   b) providing at least one second double stranded DNA fragment having at least one terminal single stranded overhang having from about 20 to about 30 bases complementary to an overhang of a);
   c) providing at least one third double stranded DNA fragment having at least one terminal single stranded overhang having from about 20 to about 30 bases complementary to an overhang of b); and
   d) mixing said first, second and third DNA fragments in a molar ratio of from about 1:1 to about 1:50 under conditions suitable to promote specific joining thereof.

20. The method of claim 19 wherein more than three DNA fragments are joined.

21. The method of claim 19 wherein the single stranded overhangs of the first, second and third double stranded DNA fragments each have from 21 to 30 bases.

* * * * *

UNITED STATES PATENT AND TRADEMARK OFFICE
CERTIFICATE OF CORRECTION

PATENT NO.    : 6,372,429 B1
DATED         : April 16, 2002
INVENTOR(S)   : Gil Sharon, Theodor Morel Fishler and Salomone Antebi It is certified that error appears in the above-identified patent and that said Letters Patent is hereby corrected as shown below:

Title page,
Item [73], Assignee, "Gesher Israel" should read -- Gesher-Israel --.

Column 11,
Line 45, "TaQ" should red -- Taq --.

Column 18,
Lines 48, 50 and 52, "Cm B" should read -- CmB --.

Column 25,
Line 24, delete "846".

Column 26,
Line 49, "Coll" should read -- ColE1 --.

Column 29,
Line 24, "32" should read -- = --.

Column 52,
Line 27, "6" should read -- 5 --.
Line 45, "8" should read -- 6 --.
Line 45, "more than" should read -- at least --.

Column 53,
Line 18, "having" should read -- each have --.

UNITED STATES PATENT AND TRADEMARK OFFICE
CERTIFICATE OF CORRECTION

PATENT NO. : 6,372,429 B1
DATED : April 16, 2002
INVENTOR(S) : Gil Sharon, Theodor Morel Fishler and Salomone Antebi It is certified that error appears in the above-identified patent and that said Letters Patent is hereby corrected as shown below:

<u>Column 54,</u>
Line 8, "of" (first occurrence) should read -- for --.

Signed and Sealed this

Eighth Day of October, 2002

*Attest:*

*Attesting Officer*

JAMES E. ROGAN
*Director of the United States Patent and Trademark Office*